United States Patent [19]

Tometsko

[11] Patent Number: 5,229,265
[45] Date of Patent: Jul. 20, 1993

[54] PROCESS FOR ANALYZING CLASTOGENIC AGENTS

[75] Inventor: Andrew M. Tometsko, Rochester, N.Y.

[73] Assignee: Litron Laboratories, Rochester, N.Y.

[21] Appl. No.: 492,584

[22] Filed: Mar. 13, 1990

[51] Int. Cl.$^5$ .................. C12Q 1/68; C12Q 1/02; G01N 33/555; G01N 33/579

[52] U.S. Cl. .................................. 435/6; 435/29; 436/519; 436/520; 436/63; 436/164; 436/172; 436/174; 436/800

[58] Field of Search .................. 436/519, 63, 94, 800, 436/164, 172, 174, 520; 435/6, 29

[56] References Cited

U.S. PATENT DOCUMENTS

| | | | |
|---|---|---|---|
| 4,668,618 | 5/1987 | Thornthwaite | 435/6 |
| 4,727,020 | 2/1988 | Recktenwald | 436/519 |
| 4,971,917 | 11/1990 | Kuroda | 436/519 |
| 5,047,321 | 9/1991 | Loken et al. | 436/519 |

OTHER PUBLICATIONS

Hutter et al., Histochemistry 75:353–362 (1982).
Labidi et al., Exp. Cell Res. 173:617–627 (1987).
MacGregor et al., Mut. Res. 189:103–112 (1987).
MacGregor et al., Envir. Mut. 2:509–514 (1980).
MacGregor et al. Mut. Res. 120:269–275 (1983).

Primary Examiner—Margaret Moskowitz
Assistant Examiner—Stephanie W. Zitomer
Attorney, Agent, or Firm—Hodgson, Russ, Andrews, Woods, & Goodyear

[57] ABSTRACT

Genotoxic chemicals are an existing wide-spread health hazard to the human population. Advances in genetic toxicology testing have made it possible to assay potential mutagens, carcinogens, teratogens and clastogens in the environment. The mouse micronucleus assay provides an example of an excellent test for genetic damage to cells. When chromosome breaks occur in the blood stem cell population, the damaged piece of chromosome remains behind as a micronucleus in the normally DNA deficient red blood cells. However, currently available manual micronucleus assays are costly, time consuming, and labor intensive. In addition, the statistics are often marginal since the number of micronucleii (MNs) in 1000 polychromatic cells are scored manually, yielding limited amounts of data. This invention discloses the means for assaying the change in micronucleated cells by high speed flow cytometry. In this procedure, cells are streamed at high speed (2500 cells/second) through a laser beam whereupon the fluorescence emission and light scatter properties of each cell are obtained. The invention discloses the procedures for dosing mice, obtaining blood samples, fixing and staining cells, configuring the flow cytometer for MN analysis, the mode of data acquistion and analysis. Internal and external quality controls are also described that are routinely used to optimize the flow cytometer conditions and permit the evaluation of the fidelity of data in real time. This process permits the analysis of 1,000,000 total cells for each sample in minutes, and it removes the subjective judgement of the manual method. In addition to vastly improved statistics, the sensitivity of the assay is significantly improved with this process.

47 Claims, 11 Drawing Sheets

Flow Cytometer Alignment with *P. berghei*

Flow cytometer Alignment with *P. berghei*

Initial Blood Sample Stained with Hoechst 33258

Final Blood Sample Stained with Hoechst 33258

Initial Blood Stained with Hoechst 33258 and PI

Final Blood Stained with Hoechst 33258 and PI

PROCESS FOR ANALYZING CLASTOGENIC AGENTS

FIELD OF THE INVENTION

This invention relates to a process for analyzing the ability of chemicals and radiation to cause chromosomal breaks in mammalian cells. The invention is directed to the fields of genetic toxicology and medical sciences where a need exists for a rapid, sensitive and economical method for evaluating clastogenic agents. It details a sensitive flow cytometry based process for the rapid analysis of changes in micronucleated cells in blood and bone marrow preparations caused by clastogenic agents.

BACKGROUND OF THE INVENTION

The in vivo micronucleus test is a method devised primarily to screen chemicals for chromosomal breaking (clastogenic) activity (Schmid, W. (Mutation Res. 31, 9 (1975)), Salamone, et al., Morris (Mutation Res. 74, 347 (1980)), Heddle, J. A., et al. (Mutation Res. 123, 61(1983)), Salamone, M. F. and Heddle, J.A. Chemical Mutagens (F. J. de Serres, ed., Plenum Press) 8, 111 (1983)). The test is based on the observation that mitotic cells with chromatid breaks or chromatid exchanges exhibit disturbances in the anaphase distribution of their chromatin. After telophase, this displaced chromatin can be excluded from the nuclei of the daughter cells and is found in the cytoplasm as a micronucleus. Blood cells provide a sensitive model for evaluating clastogenic events since the nucleus of the erythrocyte stem cell is expelled a few hours after the last mitosis yielding DNA deficient cells. Treatment with clastogens or spindle positions which cause chromosomal breaks in the stem cell result in the formation of easily detectable micronuclei (MNs) in these anucleated young polychromatic erythrocytes (PCEs). These young anucleated cells are still rich in RNA and, therefore, exhibit unique staining patterns that distinguishes them from the mature normochromatic erythrocytes (RBCs). For example, when blood is stained with a metachromatic dye such as acridine orange (AO) (Hayashi, M., et al. (Mutation Res. 120, 241 (1983)), the DNA of a micronucleus exhibits a bright green-yellow fluorescence. In contrast the young RNA rich anucleated PCEs exhibit red fluorescence when stained with AO and excited with a 488 nm light source. The RNA rich polychromatic cells (PCEs) find their way into the blood stream and eventually complete their evolution to the RNA deficient and nonfluorescent normochromatic red blood cells- the mature RBCs. The brief existence of the PCE cells (about 48 hrs) has been used by practioners of the art to define the time frame for the conventional micronucleus assay by counting only MN in the PCE population. This invention offers a more flexible analysis timeframe which is not dependent upon the PCE population and allows for a choice of assay times ranging from hours to weeks. Although bone marrow was used in the original micronucleus assay, McGregor et al. (Environmental Mutagenesis 2,509 (1980)) demonstrated that the micronucleated PCEs and RBCs accumulate in peripheral blood of mice following treatment with a clastogen. Blood provides a good supply of test material for the micronucleus test. The spontaneous background level of aberrations in blood or bone marrow cells is usually quite low (i.e. about 2 MN/1000 PCEs). Clastogenic agents can cause an increase in the relative number of micronuclei present.

The micronucleus test provides a relatively rapid and sensitive indicator of both chromosomal aberrations and chromosomal loss that leads to numerical chromosome anomalies. However, the conventional method of carrying out the test with bone marrow cells has inherent limitations. Femurs are the usual source of bone marrow cells, and it has been necessary to use large numbers of animals (e.g. 50–60 mice per test substance; 10 mice/set) in order to overcome variations between animals. One set of mice must be used as a control to determine the spontaneous MN background level which is then used as a baseline for measuring a clastogenic response. This manual test involves the preparation of large numbers of slides, followed by hand scoring the number of micronuclei present in 1000 polychromatic cells. The scoring operations are subject to human errors aristing from the level of experience of each technician. Statistical errors also occur due to the relatively small number of cells that are processed in the manual scoring mode. Manually scoring the slides for a single test substance requires days of cell counting, resulting in considerable level of fatigue which can also lead to inaccuracies. With current state of the art, a conventional micronucleus test requires 8–12 weeks to complete, and it is both tedious and labor intensive. Because of the low number of cells scored (1000 PCEs) in a manual micronucleus assay, the statistics obtained are usually marginal. Practitioners in the art realize the need for improved sensitive methods for analyzing micronucleated cells. One possible method of automation is high speed flow cytometry (FCM).

In the FCM process, cells pass in single file through a laser beam where their fluorescence and light scatter characteristics are determined. Instead of scoring only 1000 cells as with manual methods, the flow cytometer is able to routinely process 2000–5000 cells/second and can analyze the number of micronucleated cells and polychromatic cells in more than 1,000,000 total cells in a few minutes. Once the experimental conditions are optimized, the statistics of the assay is related to the number of cells processed, and as a consequence greater accuracy in scoring chromosomal aberrations can be achieved. In 1982, Hutter and Stohr ( Histochemistry 75,353 (1982)) made an attempt to apply flow cytometric analysis to the micronucleus assay. Using bone marrow cells, along with a DNA-specific fluorochrome (DAPI; 4'-6'-diamidino-2-phenylindole) and a fluorescent protein stain (SR101; sulforhodamine 101), they identified flow cytometry patterns of putative micronucleated cells. However, their method was not able to discriminate normochromatic (mature) from polychromatic (young) erythrocytes and the flow cytometer cell counts did not correlate well with hand counts. The current state of the art is further defined by the fact that an Automated Micronucleus Scoring Workshop was held in November, 1988 at Miliptas, Calif., sponsered by the Environmental Mutagen Society to Evaluate the feasibility of automating the micronucleus assay, using flow cytometry or image analysis process, further demonstrating that a suitable flow cytometry based MN assay is not presently available. No definitive methods were forthcoming from this meeting, but the underlying difficulties of automated micronucleus scoring were addressed. Thus, although it is clear that a need exists for scoring larger numbers of micronulceated cells, the means for achieving automation is not presently known to Practitioners in the art.

The development of an FCM based micronucleus assay has been difficult becuase the process requires optimization of conditions in the biological, chemical, instrumentation and analysis disciplines. In order to be functional, the process must deal with the fact that micronucleated cells are present in blood or bone marrow samples as rare events. The micronuclei are small in comparison to the parent nucleus and cover a considerable range from 0.5 to about $2\mu m$ in diameter depending upon the position of a chromosomal break. Similarly, PCE staining is an experimental variable, since the RNA of a PCE is degraded over time and the fluorescence yield of a PCE is related to its age. A functional FCM based micronucleus process must deal with the specific limitations and requirements of a flow cytometer. For example, the cells must be fixed in a way to minimize aggregation and permit the cells to pass through the laser beam in single file. Cell fixation is critical since it will influence the morphology and staining properties of cells, as well as the resolution of cell population during FCM analysis. Some cell fixation methods such as those that use glutaraldehyde or paraformaldehyde result in increased autofluorescence which can be undesirable for an FCM based micronucleous assay. The cell staining process must also be optimized because the amount of DNA in the micronucleus is quite low. Since the conventional assay evaluates the number of micronuclei per 1000 PCEs, differential staining of micronuclei and PCEs could be required. The dyes employed in the assay must also be chosen to provide maximum fluorescent signal, reflecting the DNA and/or RNA content of a cell, and must be able to absorb light at the wavelength provided by the laser beam(s). A means must also be provided for optimizing the signal output of a micronucleus by the use of suitable filters and gains on the acquisition photomultiplier tubes (PMTs), as well as a means for acquiring data for the cells of interest. The data must be processed in order to highlight any changes that might occur in the micronucleus and/or PCE population. Finally, the process should provide reproducible results which accurately reflect the content of micronucleated cells in each sample. The purpose of this invention is to disclose a process for effectively analyzing changes in the micronucleated cell populations in the blood and bone marrow cells caused by the action of clastogenic agents.

BRIEF SUMMARY OF THE INVENTION

This invention is a flow cytometry (FCM) based process for analyzing changes in the micronucleated cell population in blood and/or bone marrow samples, due to the action of chromosomal breaking (clastogenic) agents. A suitable process is not presently available due to the multidisciplinary nature of the needed technology. Chemical, biological, instrumentation and data processing aspects of the disclosed methodology are presently unknown. Accordingly, the invention provides details concerning sample preparation, instrument configuration, the analysis mode for favorable results, and a sensitive means for extracting the change in micronucleated cells from the data. The process is able to analyze 1,000,000 blood cells per blood sample in minutes, in contrast to hours required to manually score said cells. Due to the larger number of events processed with this invention, the statistics of the assay are vastly improved and human scoring errors are essentially eliminated.

A BRIEF DESCRIPTION OF THE DRAWINGS

FIG. 1A. A bivariate graph of red fluorescence versus blue fluorescence is shown for Plasmodium berghei was fixed and stained with Hoechst 33258. Cells with a nucleus have been gated out (Dots 15; Contours=25,50,75,100,200,400,600,800,1000).

FIG. 1B. A bivariate graph of red fluorescence versus blue fluorescence is shown for P. berghei infected blood that was stained with Hoechst 33258 and propidium iodide (PI). (Dots-15; Contours=25,50,75,100,200,400,600,800,1000).

FIG. 2A. A blue fluorescence histogram is shown for P. berghei infected blood that was fixed and then stained with Hoechst 33258 and propidium iodide (PI). PMT gains were adjusted so as to position the peak of channel 264.

FIG. 2B. A red fluorescence histogram is shown. This P. berghei infected blood sample as fixed and then stained with Hoechst 33258 and propidium iodide (PI). The gains on the red PMT were adjusted so as to set the peak at channel 432.

FIG. 3. A forward light scatter histogram is shown. A set of gates is routinely used to bracket the blood cell populations. In this way, undesirable debris is gated out and is not included in data acquisition.

FIG. 4. A bivariate graph of polycyhromatic cells (PCEs) and micronucleated cells (MNs) is shown. The cells were fixed and stained with Hoechst 33258 and propidium iodide. The red threshold was set at 304 to gate out RBCs.

FIG. 5A. A red fluorescence histogram is shown for an initial (t=0) blood sample that was stained with Hoechst 33258 and propidium iodide. The location of the PCE and RBC peaks is shown. The vertical lines show the analysis area and gave the PCE events shown in Table 1 were obtained from this gate range.

FIG. 5B. A red fluorescence histogram is shown for a 96 hour blood sample obtained from the same mouse as shown in 5A. This mouse was dosed with methyl methanesulfonate (MMS) at 0 and 48 hours. Note the rise int he PCE profile in the 96 hour sample, presumably due to the initial bleeding. This change was used to calculate the factor, K, in Table 1.

FIG. 6A. A red versus blue fluorescence bivariate graph is shown for an initial (t=0) blood sample. The contours for RBCs and micronucleated cells (MNs) are clearly resolved. An analysis area similar to that of FIG. 1A is shown. Sample size=500,000 cells. Dots=15; Contours=20,25,30,60,90,120,150,180,210. (Control for FIG. 6B).

FIG. 6B. A red versus blue fluorescence bivariate graph is shown for a blood sample that was obtained at 96 hours. This mouse was dosed with MMS (100 $\mu g/g$ body wt) at 0 to 48 hours. Note the increase in the number of MNs in the analysis area relative to the initial blood (i.e. FIG. 6A). (Dots=15; Contours=20,25,30,60,90,120,150,180,210).

FIG. 7A. A red versus blue bivariate graph is shown for an initial (t=0) blood sample that was stained with Hoechst 33258 and propodium iodide. The RNA rich PCEs are evident in this profile, and two analysis areas are shown. Sample size=500,000 events. Dots=15; Contours=20,25,30,60,90,120,150,180,210. (Control for FIG. 7B).

FIG. 7B. A red versus blue bivariate graph is shown for a final (t=96 hour) blood sample that was fixed and then stained with Hoechst 33259 and propidium iodide. This mouse was dosed with MMS (100 μg/g body wt) at 0 to 48 hours. Analysis areas show the numbers of PCEs and micronuleated cells (MNs) and can be compared with control blood (FIG. 7A).

FIG. 8. A blue fluorescence histogram of P. berghei infected blood is shown. The blood was fixed and stained with Hoechst 33258. A primary analysis window is shown along with seven smaller windows to the left of the primary that were used to show the distribution of cells if the primary window were extended to the left.

FIG. 9A. A blue fluorescence histogram for an initial (t=0) blood sample is shown. The blood was fixed and then stained with Hoechst 33258. The primary analysis window contains 791 MN events. Seven additional windows are shown. Their contents from right to left are listed in Table 5, along with the increase in MNs as these events are added to the primary window values.

FIG. 9B. A blue fluorescence histogram for a 96 hour blood sample from a mouse that was dosed with cyclophosphamide (CP; 100 μg/g body wt) is shown. The blood was fixed and then stained with Hoechst 33258. The primary analysis window contained 1360 MN events. Seven additional windows are shown. Their contents from right to left are listed in Table 5.

FIG. 10. A bivariate graph of red fluorescence versus blue fluorescence is shown for a P. berghei infected blood sample. PC-microspheres exhibit a high red an a moderate blue fluorescence signal that can be used to monitor the flow cytometer before data is acquired for each sample. The fixed cells were stained with Hoechst 33258.

FIG. 11. A red fluorescence versus blue fluorescence bivariate graph is shown for an MN rich blood sample. Instrument stability is routinely determined by monitoring the location of the peak and the shape of the contour patterns for microspheres and CRBC which are added to said samples, or for the internal nucleated cells which are normally present in said samples.

FIG. 12. The channel location of the PC-microsphere peak was determined relative to the location of the profile of RBCs infected with P. berghei. Incorporated of these microspheres into each sample permits the routine evaluation of changes in instrument response or charges in fluorescence emission due to specific conditions that might affect stain response.

FIG. 13. The location of PC-microsphere was determined relative to the P. berghei infected red blood cell peak. Incorporation of microspheres in unknown samples permits a fast check on instrument alignment to insure good quality control during data acquisition.

FIG. 14. Two mice at each point were dosed at 0hr and 48 hrs with cyclophosphamide (CP) at the concentrations shown. A t=0 and a t=96 hour blood sample was obtained for each mouse. After fixing and then staining the cells with Hoechst 33258, the number of MNs per one million total cells were determined. The number of t=0 MNs was substracted from the t=96 hr value. The duplicate samples were averaged and plotted. For comparison, the 96 hour samples were also hand counted and the average number of MNs/1000 PCEs at each dose was plotted on this same graph.

DESCRIPTION OF THE PREFERRED EMBODIMENT(S)

Figure 1A:
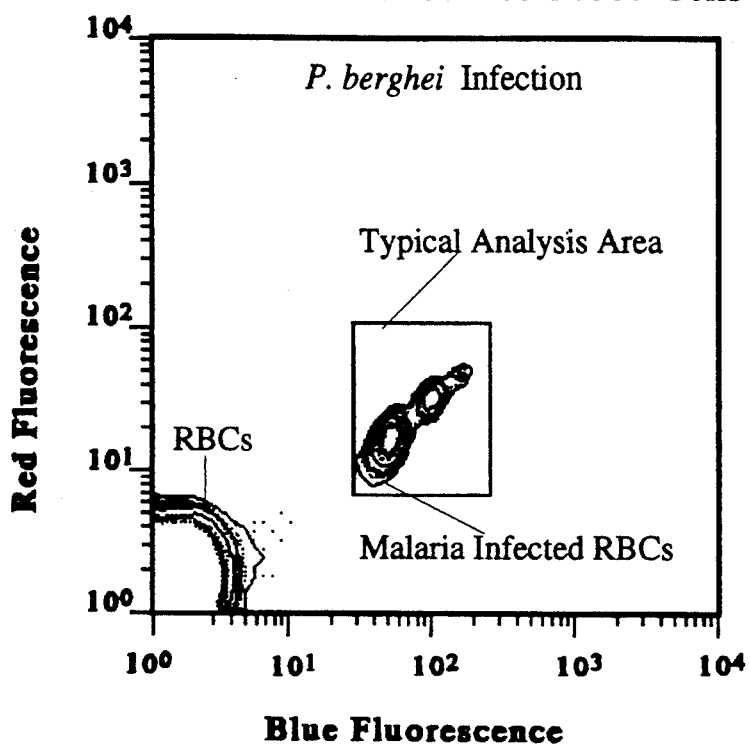

The process of this invention is broad in scope and, consequently, the preferred embodiment must cover the interplay of different scientific disciplines which lead to an effective and reproducible flow cytometry based micronucleus assay. Accordingly, the description herein will directly parallel the operation that would be carried out in a typical micronucleus assay.

THE NEED FOR A BIOLOGICAL MODEL

Because they are rare and heterogeneous, micronucleated cells (MN-cells) and polychromatic cells (PCEs) are unsuitable for optimizing the chemical and analtyical aspects of this process. Micronuclei are located in the red blood cell population and are characterized by the presence of a small DNA component which can vary in size from 0.5 μm to about 2 μm in diameter. Micronucleous DNA comprises a small fraction of the total DNA present in the stem cell before explusion of the nucleus and it is distributed over about a one log range of fluorescence during flow cytometric analysis. A similar heterogeniety is present in the RNA rich polychromatic cells(PCEs). PCEs are the immature red blood cells that result immediately after the expulsion of the nucleus. These cells are usually deficient in DNA, but still contain a significant amount of RNA which decreases over a 48 hr period during the PCEs evolve into the mature red blood cells (RBCs). Because of their wide variation in RNA content, PCEs are also unsuitable for routine optimization purposes. Consequently, another biological model with the general characteristics of Mn-cells and PCEs was needed to expedite the development of flow cytometry based mouse micronucleus assay. In the development of the present invention, it was found that the malaria parasite, P. berghei, provides an excellent model for optimizing cell fixing, cell staining, and instrument calibration. The DNA content of the parasite is genetically determined and is within the size range of a micronucleus. P. berghei also contains RNA and the staining pattern of the infected cells is similar to stained PCEs. Finally, this malaria parasite accumulates in the red blood cells, which are the cells of interest for the micronucleus assay. The parasites are actively reproducing within the RBCs and P. berghei infected cells can make up 10–20% of the red blood cell population. For these reasons, blood from P. berghei infected mice has been used routinely in the optimization procedures described herein.

FIXING BLOOD CELLS FOR FCM ANALYSIS

The fixation procedure can affect the permeability of a cell, cell morphology and the amount of undesirable autofluorescence that is associated with a cell preparation. Fixing procedures can cause changes in cell structure (that are reflected in the light scatter patterns) as well as changes in the distribution of the dye molecules within the cells (resulting in altered fluorescence emission patterns). Practioners of the art are unaware that fixing the cells at ultralow temperatures circumvents these fixation problems and provides cells that are suitable for subsequent staining and FCM analysis. Initially, the cells are centrifuged in order to separate them from serum components which could aggregate when added to cold fixative. To fix cells, a fresh blood sample (25 μl) containing an anticogulant is suspended in a solution containing 1% BSA and 10% dimethylsulfoxide (DMSO) in PBS (2 ml). The cells are centrifuged at 500×g for five minutes at room temperature. The supernatant is discarded and the pellet is resuspended in the small amount of residual supernatant that remains. This cell suspension is cooled to 0° C., the cells are diluted further with cold (−70° C.) absolute methanol (2 ml) and it is incubated at −70° C. for five minutes. The cell suspension is then immediately diluted with 1% BSA in PBS (10 ml) and is centrifuged at 500×g for 5 minutes. The low temperature treatment yields fixed cells with good morphology as viewed with either inverted phase contrast microscopy or fluorescent microscopy. Autofluorescence of these cells is very low, in contrast to glutaraldehyde or paraformaldehyde fixation procedures that are widely used in the art. Other volumes of blood and/or BSA in PBS are also compatible with this cell fixing process. The volume of methanol should be in the range of 0.5 to 20 ml. The temperature of the methanol should be in the range −30° C. to −90° C., and the fixation time in the range of 1 minute to 60 minutes for good results. When cells are fixed in alcohol at higher temperatures (e.g. in the range of +37° C. to −20° C.), they tend to aggregate and quickly settle to the bottom of the centrifuge tube. In contrast, cells fixed at −70° C. act like colloidal particles in that they stay in suspension and do not have a tendency to settle. Other ultra cold solvents can be used in place of methanol, such as acetone, methanol/acetone solutions, etc.. Two fixed cell samples can be prepared for each mouse, an initial (time=0) sample and a final time=96 hr sample. Cells fixed in this way can be stored at 0° C. for weeks with no significant deterioration and are ready for staining and MN analysis.

CELL STAINING

It is known to practioners in the art that a variety of fluorescent dyes can be used to stain the DNA and RNA of cells. Even so, the specific stain, combinations or staining conditions that are optimum for the FCM based micronucleus assay are unresolved. I have found that good results are obtained with the micronucleous assay when Hoechst 33258 is used as a DNA stain and propidium iodide (PI) is used as the RNA stain. These dye can be used individually or together to stain different cell populations. By choosing proper concentrations of these two dyes in conjunction with 363 nm excitation wavelength, it is possible to obtain a blue fluorescence signal from the Hoechst 33258 labeled micronucleii. A red fluorescence signal can be obtained from propidium iodide labeled PCEs. Whereas neither the dye combination, the dye concentration, the dye excitation wavelengths nor the appropriate buffer systems are known to practitioners in the art for an FCM based micronucleus assay, the following staining protocal is submitted as an embodiment of the present invention. A 10× stock solution of the dye should be prepared by dissolving 14.3 mg Hoechst 33258 in methanol (100 ml). A working solution is then prepared by adding 0.25 ml of the 10× stock solution to 9.75 ml of complete Sorensen's buffer. This working solution is then passed through an 0.2 micron acro-filter disk (Gelman Sciences) to remove any debris. The filtered working solution is further diluted by adding 25 μl to 967.5 μl of saline buffer (9 g NaCl and 0.445 g sodium bicarbonate per liter). The fixed cells that have been stored as a pellet at 0° C. should be suspended in the residual cell pellet fluid by tapping the bottom of the centrifuge tube. A sample of these fixed cells (15 μl) is added to 992.5 μl of the buffer-dye solution in each corresponding test tube. By preparing a large amount of the buffer-dye solution, all samples can be subjected to the same staining conditions. When blood from a malaria (*P. berghei*) infected mouse was fixed and stained by this procedure, the bivariate pattern shown in FIG. 1A was obtained, exhibiting a strong blue fluorescence and a weaker red fluorescence signal. A typical analysis area is shown in FIG. 1A wherein MNs should be found if *P. berghei* infected cell are a suitable model for the micronucleus assay. It will be evident from later figures that micronucleated cells are indeed found in the same region of the bivariate graph as the malaria infected RBCs under these staining conditions.

When two dyes are used for simultaneous micronucleus and PCE discrimination, the cell suspension is prepared as follows: The Hoechst 33258 working solution described above is prepared and is filtered through an 0.2 micron Acro-disk (Gilman Sciences). In addition, a propidium iodide (PI) working solution is prepared (5 mg PI/100 ml phosphate buffered saline (PBS)). A buffer-dye solution is then prepared by adding the PI solution (100 μl) and Hoechst 33258 working solution (25 μl) to PBS (867.5 μl). The resulting buffer-dye solution is then dispensed (992.5 μl) into samples tubes. A sample of fixed blood (15 μl) is then added to the corresponding tube. When blood from a malaria (*P. berghei*) infected mouse was fixed and stained by this procedure, the bivariate pattern shown in FIG. 1B resulted, in which a stronger red fluorescence signal was obtained. In this case, good resolution is achieved if BSA is omitted from the stained cell suspension. The pH of the stained solution is important for good fluorescence emission profiles and resolution of the different cell populations. With Hoechst 33258 and propidium iodide, good results can be obtained in the range from pH 6 to pH 8. Lower or higher pH levels cause a broadening of the fluorescence patterns which adversely affect the resolution of the PCes and micronucleated cells. Operationally, it is advisable to store the fixed samples and analyze freshly stained samples.

INSTRUMENT CALIBRATION WITH MALARIA

Figure 2A:
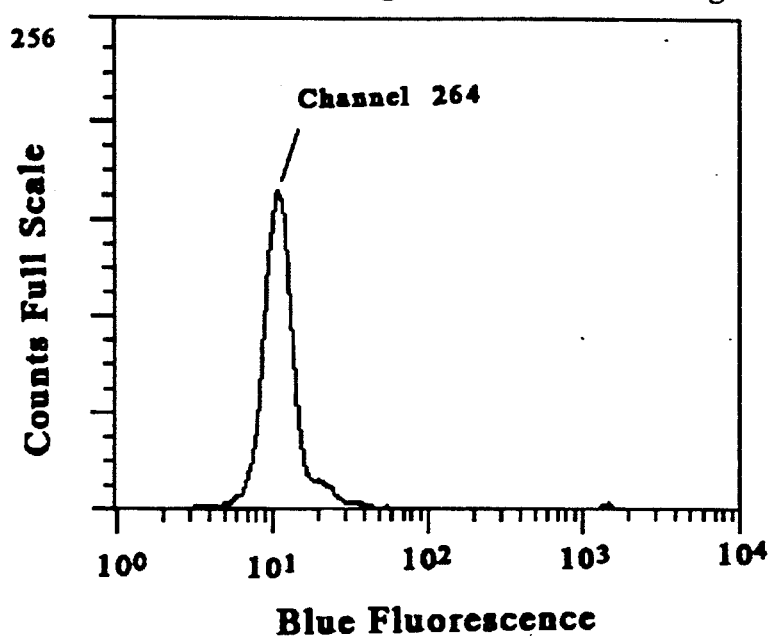
Figure 2B:
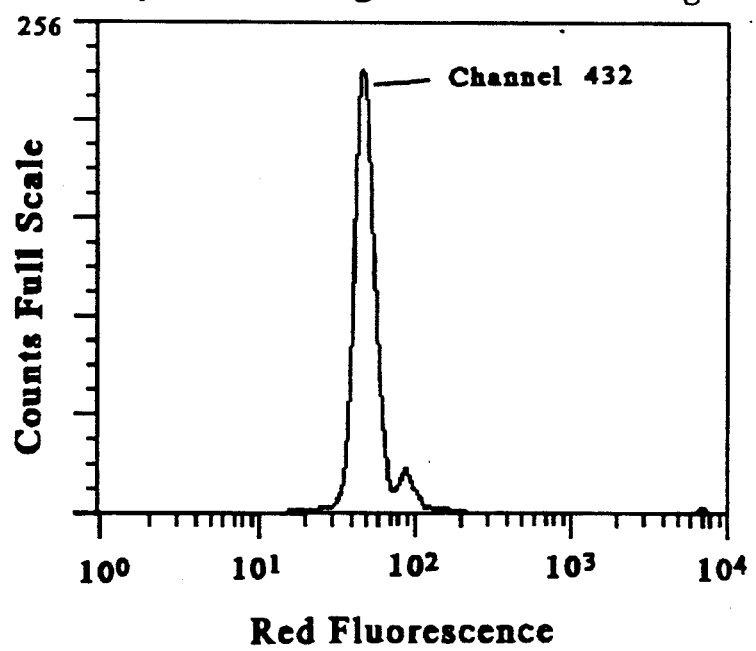

The analysis of said fixed and stained cells relies further upon properly setting and adjusting the flow cytometer for micronucleus analysis. Again, the *P. berghei* infected blood provides a good control. Since the DNA content of the parasite is regulated by genetics, any RBCs that contain a single parasite will give a similar fluorescent signal when analyzed by flow cytometry, and results in relatively sharp fluorescent peaks that can be used to align the flow cytometer each day (FIGS. 2A and 2B). The parasitized blood is stained in parallel with the test samples, so that an adjustment in the flow cytometer settings can be made in order to compensate for subtle changes in cell staining. Even if different laser powers are used, alignment of the peak of the parasite fluorescence profile specific channels on histograms can be achieved by adjusting the PMT gains so as to superimpose the peak over any chosen alignment channel as shown in FIG. 2. Fixed and stained malaria blood can thus be used to compensate for subtle variations in the conditions and settings of the flow cytometer where changes in laser power, beam alignment, signal to noise ratio, marginal filters, dirty optics or brewster windows, etc. might require recalibration of the instrument. Fluorescent microspheres are also used for instrument alignment purposes and to check for instrument drift during the analysis of multiple samples. However, they do not permit compensation for staining variations which is possible with P. berghei infected blood cells and nucleated blood cells. Opertionally, when the malaria blood is fixed and stained with Hoechst 33258 and propidium iodide as described above, the blue fluorescence peak can be routinely set at a specific channel (e.g. channel 264) while the red fluorescence peak can be set at another channel (e.g. channel 432), on the blue fluorescence and red fluorescence histograms, respectively (FIGS. 2A and 2B). Positioning of the parasite peaks at selected locations can be accomplished for other dyes or dye combinations using proper PMT gains. By using appropriate biological models for alignment, it is possible to achieve greater reproducibility and more accurate comparison between experiments by providing similar signal processing condition with the flower cytometer.

FLOW CYTOMETER SETUP

Figure 3:
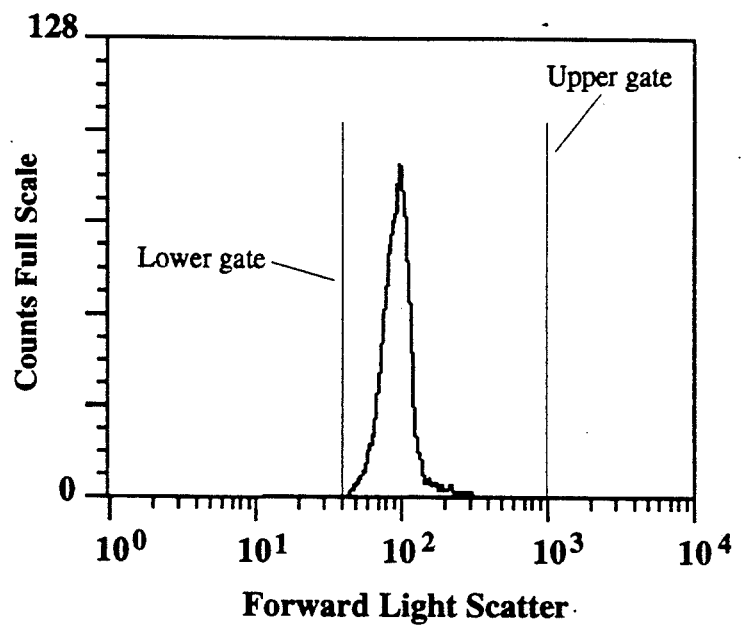
Figure 4:
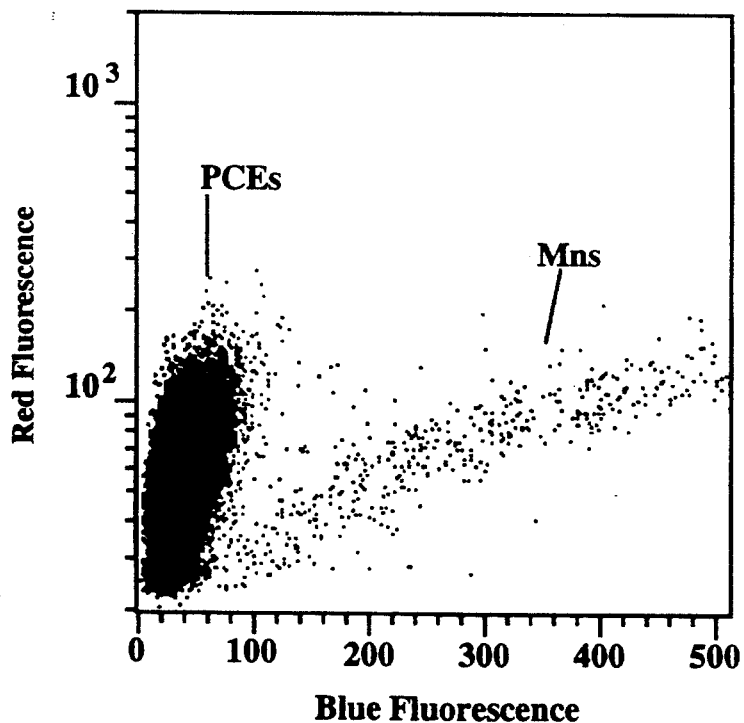

Optimum flow cytometer settings are extremely important in this process since the signal from a micronucleus is relatively low. The micronucleus and PCE signals should be pulled as far away from the electronic background noise as possible. In order to obtain sufficient signal from the malaria parasites and from micronucleated cells using the Hoechst 33258 stain, proper filters must be placed before the blue fluorescence and red fluorescence photomultiplier tubes (PMTs). In accordance with the methods of the present invention, a good blue-green signal can be obtained for micronucleii and the malaria parasites if a 400 nm long pass filter and a 555 nm short pass filter is placed before the blue-green PMT. This configuration allows maximum fluorescence emission from the tiny micronucleus to reach this PMT. It is possible to use tighter filter windows by using narrower band pass filters. However, by narrowing the window, certain configurations will drive the fluorescence emission signals into the background noise. In accordance with the methods of the present invention, a 580 nm long pass filter in front of the red PMT gives good results, and the gains can be adjusted to place the P. berghei red fluorescence peak at channel 432 on the red fluorescence histogram as shown in FIG. 2b. The signals received by the PMTs or the light scatter photodiode can be processed as peak height, area, pulse width or ratio modes to highlight the micronucleated cells and PCEs in each sample. The data presented herein were obtained in the peak height configuration. Similarly, the data may be acquired and processed as either linear or log signals. In one configuration of the invention (e.g. FIG. 1), logrithmic data were acquired for the forward light scatter, the 90° side scatter and the red and blue fluorescence peak height signals. In order to isolate the PCE and MN populations, a signal gate is usually placed on either side of the forward light scatter signal as shown in FIG. 3. In some cases, the upper gate is brought in to the edge of the major light scatter peak. This gate set insures that the acquisition of fluorescence information will be from cells and not debris. Nonfluorescent RBCs are the predominant blood cell population, and in some cases, it may be desirable to elimate them for acquisition. These cells can be excluded by either setting a red fluorescence software gate above the RBC peak, or by triggering on red fluorescence and setting the trigger threshold above the RBC signal position. Although the exact position of the red threshold is arbitrary, a red fluorescence trigger threshold of 304 (i.e. a threshold slightly above the first log hash mark) gives a good descrimination level wherein PCEs and nucleated cells are readily acquired while RBCs are excluded. FIG. 4 shows an expanded bivariate dot pattern that is obtained with this threshold configurations when red fluorescence is logrithmic and blue fluorescence is plotted linearly. Good separation and resolution of PCEs and MNs is obtained.

LASER BEAM CONSIDERATIONS

Figure 1B:
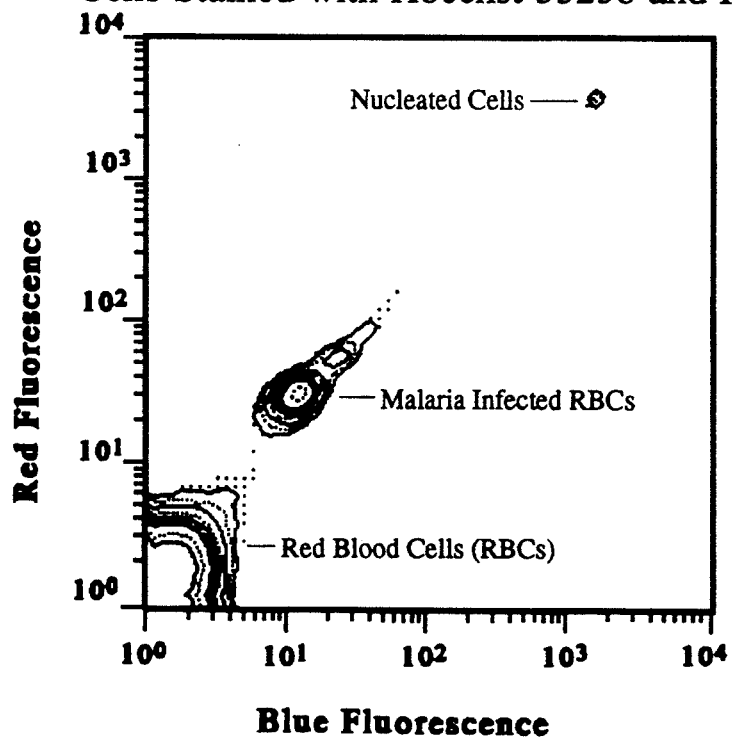

In accordance with the method of the present invention, was used a 363 nm beam from a 5 watt argon ion laser in conjunction with a FACStar Plus flow cytometer (Becton-Dickenson) to interrogate the cells as they stream through said beam. One configuration of the invention is to use a 20 µm elliptical beam, that is focused on the sample stream: The results and analysis described herein were obtained with said beam. Different beam shapes are also acceptable, including a 20 µm spherical beam, 50 µm sperhical beam, 16 µm elliptical or spherical beams or 5 µm elliptical or sperical beams, etc. Other lens configurations are also acceptable to practice this invention. However, appropriate adjustments in gains and amplifier settings would be required to optimize the signal under different excitation and filter conditions. The laser wavelength should be provided which will activate the DNA and/or or RNA bound stains. In one example, DNA is stained with Hoescht 33258 while RNA is stained with propidium iodide. Practitioners in the art generally use visible laser lines (e.g. 488 nm) to analyze PI labeled cells as in the case of live to dead discrimination, wherein dead cells takeup PI while live cells do not. In development of the method of the present invention it was observed that propidium iodide is readily excited with a near UV laser line tuned at 363 nm. By using a 363 nm beam, both Hoechst 33258 and PI labeled cells can be analyzed simultaneously as said cells pass through the laser beam resulting in the bivariate patterns as shown in FIG. 1B. The power output level of the laser is not critical. The studies described herein were carried out with the laser power set between 50 mW and 120 mW with similar results. A laser power of 80 mW has been used routinely. Other power levels are acceptable, from 10 to 200 mW provided that the system is adjusted properly to provide a good signal to noise ratio and proper positioning of the PCE and MN cell profiles on the red fluorescence and blue fluorescence histograms, respectively.

Another configuration of the invention involves the use of dual lasers. In this case, the beams of two lasers are focused at two separate interrogation points along the sample stream. The distance between said interrogation points may be from 20 to 200 µm depending upon the beam size and shape restrictions. In dual laser configuration, one set of PMTs processes signals that are emitted by cells passing through the first laser beam, while a second set of PMTs process signals emitted by cells as they pass through the second beam. In the case of Hoechst 33258 and propidium iodide, the first beam could be set at 363 nm, and thus accumulate data on the DNA content of said cells and would thus determine the presence of micronuclei. The second laser could provide a beam at 488 nm or higher wavelength in order to excite cells labeled with propidium iodide. Although the 363 nm emission of a single argon ion laser is sufficient to excite said dyes simultaneously, other dye combinations could be used with this invention, in order to use said dual laser mode to acquire the PCE and MN data for the sample populations. This invention is able to accommodate either single or dual laser configurations in conjunction with suitable filters before the acquisition PMTs, and it is compatible with RNA and DNA stains that are excited by either a single laser or separate laser emission at different wavelengths. The output wavelength and positioning of the first and second laser beams should be correlated with the absorption properties of the fluorescent stains and the specific acquisition configuration of the PMTs.

DATA ACQUISITION

The photomultipliers (PMTs) used for data acquisition should be sensitive enough to accumulate the relatively low fluorescence signals that are emitted by the micronucleii and the RNA of polychromatic cells. The instrument configuration used in developing this invention consisted three PMTs that sensed the red fluorescence, blue fluorescence and 90° side scatter signals. Signals from a forward scatter detector were also acquired. The general principle of the invention is compatible with multiparameter data acquisition in which multiple PMTs are used to obtain 5 to 8 parameters on each cell. Gate settings on the forward scatter and side scatter, either hardware or software, can be used to isolate said blood cells from any debris. FIG. 3 shows a forward light scatter gate that is used to focus on signals from cells. Similarly, gates or signal thresholds can be placed on the fluorescent signals so as to acquire data on specific cell populations. The rate of data acquisition by this invention is a variable that extends from 20 cells/second to 100,000 cells/second in high speed analysis. The rate of data acquisition will be determined by hardware and software consideration, as well as the abortion rate of the acquisition system. Regardless of the rate of acquisition, the number of PCEs and MNs will be tabulated in each sample, based on their unique light scatter and fluorescent emission properties. A rate of 2500 to 3000 cells/second gives a good rate of acquisition with a relatively low abort rate. A variety of computers can be used for data acquisition. This invention has used an HP-3000 computer, equipped with a 20 megabyte hard disk drive.

DEFINING THE ANALYSIS RANGE

It is known in the art that the clastogenic action of chemicals result in the formation of micronucleii in the blood cell population. The analysis boundaries for the manual micronucleus assay are determined by the lifetime of the immature polychromatic erythrocytes. The lifetime of PCEs is about 48 hour during which time they are rich in RNA, and exhibit unique staining patterns which distinguish them from the general red blood cell population. As a consequence, the manual assay procedure has focused on the PCE population as the target cells for determining clastogenic activity. This invention offers an alternative to 1) analyzing MNs in only PCE population, and 2) limiting the analysis to 48 hour time interval as defined by said PCEs. I have found that the increase in micronucleated cells in the blood at any time (t) can be determined relative to a $t=0$ blood sample that is obtained for each mouse before dosing begins. The initial blood sample serves as a background reference point for evaluating subsequent increases of decreases in the number of said micronucleated cells in samples taken at the later time. Once such a background is determined for a mouse, a final sample can be obtained from days to even weeks following the initial (i.e. $t=0$) sample.

The change in MNs, $\Delta$, can be obtained by the relationship, $$\Delta = MN96 - MN0$$

where MN0 is the initial number of MN-cells at $t=0$ and MN96 is the final number of MNs obtained after dosing where in the final blood sample was obtained 96 hrs after the initial sample. Because of this flexibility in obtaining the final sample, doses of test substance can vary from a single dose over a short time interval (e.g. 48 hr to 96 hrs) to ten or more doses over a longer time interval (weeks) in some subchronic studies. In any case, the change in the number of micronucleated cells can finally be determined relative to said background level for each individual mouse.

An important aspect of this invention is the ability to set an outer time limit for an assays window that is measured from the time when an initial blood sample is taken and/or the time when dosing with a test substance begins. The affect of dosing should then be evaluated relative to the control blood sample, and should remain close to the background level in untreated mice. Each mouse will exhibit a specific background level of micronucleated cells in its blood. When a $t=0$ blood sample is obtained, the mouse will be forced to replenish the lost blood cells by signaling the blood stem cells to produce more RBCs. The stem cells should introduce new micronucleii into the blood cell pool at the spontaneous background rate (i.e. 1-2 MNs/1000 PCEs). In the absence of a clastogen, one would expect to see the number of MNs/million total RBCs as relatively constant when comparing the $t=0$ and the $t=96$ hr control samples. To show the effect of obtaining the initial blood sample on the number of MNs at a later time in an untreated animal, a control experiment was carried out. In this experiment, an initial blood sample was obtained from two mice (A and B) which was then dosed with 0.9% saline at 0 hr and at 48 hrs. A final blood sample was obtained at 96 hrs. These samples were fixed and stained with Hoechst 33258 as described earlier. The samples were then analyzed with the flow cytometer providing a 363 nm laser line (power=84 mW). In this experiment, cells were processed at a rate of 2500 cells per second and one million total cells were analyzed for each sample. In addition, each sample was run in triplicate in order to obtain a standard deviation on the data. The results of the experiment are shown in Table 1.

TABLE 1

| The Change in In Micronucleated Cells in Control Blood Samples* (Blood was obtained at 0 hr and 96 hrs)* | | | | | |
|---|---|---|---|---|---|
| Mouse A | | Difference | Mouse B | | Difference |
| $A_0$ | $A_{96}$ | $(A_{96} - A_0)$ | $B_0$ | $B_{96}$ | $(B_{96} - B_0)$ |
| 1700 | 1722 | 22 | 2065 | 2052 | −13 |
| 1711 | 1779 | 68 | 1979 | 2053 | 74 |
| 1679 | 1678 | −1 | 1983 | 2061 | 78 |

TABLE 1-continued

The Change in In Micronucleated Cells in Control Blood Samples*
(Blood was obtained at 0 hr and 96 hrs)°

|  | Mouse A | | Difference | Mouse B | | Difference |
|---|---|---|---|---|---|---|
|  | $A_0$ | $A_{96}$ | $(A_{96} - A_0)$ | $B_0$ | $B_{96}$ | $(B_{96} - B_0)$ |
| means | 1697 ± 16 | 1726 ± 51 | 30 ± 35 | 2009 ± 48 | 2055 ± 5 | 46 ± 51 |
|  | $\overline{\Delta A} = 1726 - 1697 = 29$ | | | $\overline{\Delta B} = 2055 - 2009 = 46$ | | |
|  | Average Change = (29 + 46)/2 = 38 events | | | | | |

*Mice were dosed with 0.9% Saline at 0 hr and 48 hrs, the blood cells were fixed and stained with Hoechst 33258, and 1,000,000 total cells were analyzed for micronuclei.
°Initial blood was obtained at t = 0; final blood was obtained at t = 96 hrs.

The results of this experiment shows that the change in MNs in control mice due to bleeding is very low, and is at or near zero. In this experiment the Average Change of the two mice, was about 38 events. The individual data sets can be summed and subtracted to give the change, or alternatively, the individual 0 hr and 96 hr lines can be subtracted to give the individual differences which can then be summed and averaged. The low zero difference in these control mice shows the effect of bleeding on the untreated mouse. The change in MNs between 96 hrs and 0 hrs is expected to increase if clastogens are present.

DATA PROCESSING WITH LIST MODE FILES

Data processing is an important aspect of this invention which is necessary in order to tabulate changes in the micronucleated cell population. Data can be acquired in list mode, dual parameter mode, or in single parameter mode. With list mode, the fluorescent and light scatter properties of each cell acquired and are stored, providing considerable flexibility in subsequent analysis. In contrast, the dual parameter mode acquires data on each cell, but stores the data as a channel summation. In the latter case, the unique properties of individual cells are lost in the summation. Since listmode permits a complete reconstruction of the experiment, it is preferred method for developing new procedures and will be described herein as one embodiment of this invention. Practitioners in the art have been unaware of the type of processing of flow cytometry list mode data that is effective in determining the number of micronucleated cells, and the important role the zero hour blood sample could play in subsequent analysis. At t=0 the blood contains the accumulated MNs that are associated with bot PCEs and RBCs, with most MNs being in RBCs. In one embodiment using list mode data acquisition, the total number of micronucelated cells per 10,000 PCEs at t=0 is determined. In this case the RBC data is not usually acquired due to the large storage requirements of list mode files. The number of MNs/10,000 PCEs should also be obtained for a later blood sample time (e.g. 96 hrs) to determined the effect of dosing with a potential clastogen. The initial bleeding causes changes in the steady state of the blood system. The actual number of PCEs may, therefore, increase substantially by t=96 hours, depending upon the amount of blood obtained at t=0. Therefore, as the PCE population grows, it will take a much shorter time to count 10,000 PCE events and their associated micronucleated cells, relative to the t=0 sample. Since the MNs and PCEs are counted together in this process, the relative number of micronucleated cells appears to decrease as shown in A96 (i.e. MNs at t=96 hr) in Table 2 when compared with MNs.

TABLE 2

Analysis of Micronuclei in Blood from Methylmethane sulfonate (MMS) treated and control mice per 10,000 PCEs (List Mode Data)

| Mouse Number | $MN_0$ (0 hr) | PCE Factor (K) (96 hr/0 hr)# | Experimental ($A_{96}$) ($MN_{96\ hr}$) | Theoretical ($T_{96}$) ($MN_0/K$) | Δ ($A_{96} - T_{96}$) |
|---|---|---|---|---|---|
| 1* | 411 | 2.27 | 197 | 181 | 16 |
| 2* | 473 | 4.89 | 90 | 97 | −7 |
| 3* | 290 | 3.28 | 82 | 88 | −6 |
| 4* | 339 | 3.56 | 122 | 95 | 27 |
| 5* | 510 | 5.45 | 86 | 94 | −8 |
|  |  |  |  | mean = | 4 ± 16 |
| 6° | 346 | 2.49 | 432 | 139 | 293 |
| 7° | 278 | 1.36 | 546 | 204 | 342 |
| 8° | 295 | 2.07 | 470 | 142 | 328 |
| 9° | 480 | 2.22 | 523 | 216 | 307 |
| 10° | 437 | 2.12 | 580 | 206 | 374 |
|  |  |  |  | mean = | 329 ± 32 |

$PCEs_{96\ hr}/PCEs_{0\ hr}$ (100,000 total cells were counted for each sample to determine K).
*Control mice received an IP injection of 0.9% saline.
°Mice received MMS (100 μg/g body weight; IP injection) at 0 and 48 hours.

Figure 5A:
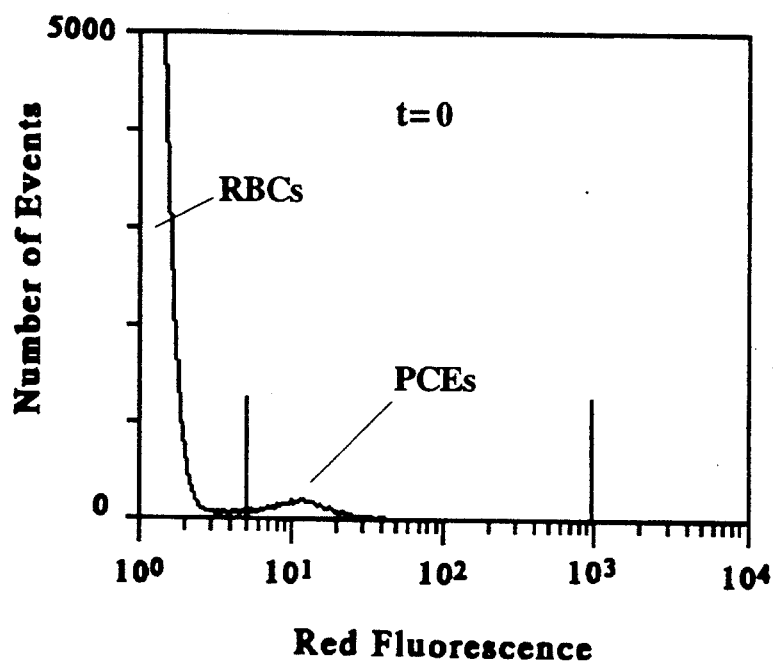
Figure 5B:
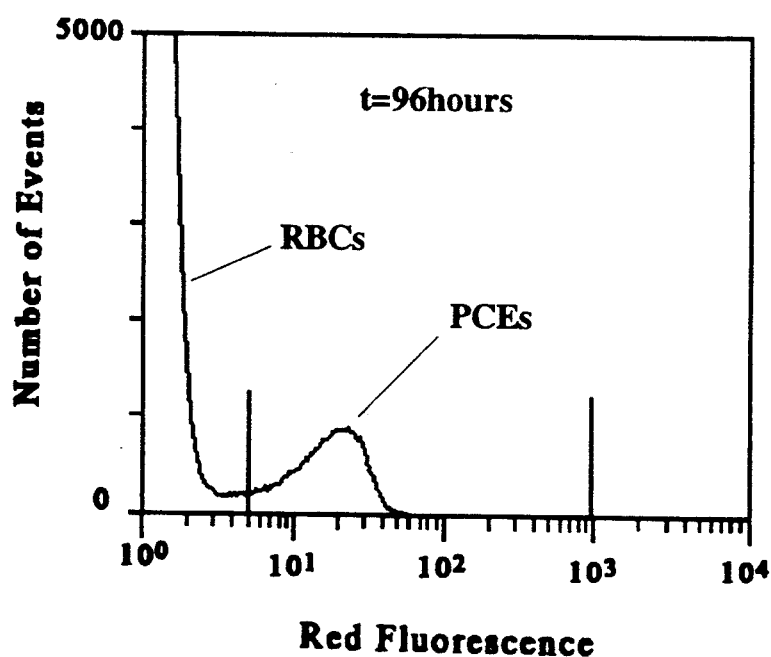

Although it is inappropriate to directly compare the number of MNs in the 0 hr and 96 hr samples because of this PCE change, it is possible to normalize the data to take into account said change. An increase in the number of PCEs will cause a decrease in the total number of MNs counted in the PCE window for a 96 hour sample. For example, consider the case wherein 400 MNs are present in the PCE population (10,000 total events) from bonctrol blood at t=0. If the PCE population doubles by t=96 hrs because of the t=0 bleeding, a 10,000 event file of the PCE population will now contain about one half as many MNs (i.e. 200-240 MNs). The background increase in MNs associated with new PCEs is expected to be at a background level in control mice or about 20-40 MNs per 10,000 PCEs. Therefore, in order to evaluate the number of new MNs produced in the assay time window, it is necessary to project the number of MNs at t=0 to any later time (e.g. 96 hours). The projected t=0 number of MNs gives a theoretical t=96 hr value (T96) for comparison with the actual MN experimental data at t=96 (i.e. A96). The adjustment factor, K, is based on the change in the PCE population that have occurred due to the t=0 bleeding. To obtain the adjustment factor the number PCEs present per 100,000 total cells are acquired in the single parameter acquisition mode at t=0 and at t=96 hours (FIGS. 5A and 5B). An analysis window is placed on either side of the PCE peak, and the factor, K, is obtained by the following relationship:

$$K = PCEs\ 96\ hr/PCEs\ 0\ hr \quad (1)$$

where the numbers of PCEs per 100,000 total cells are determined at 0 hr and 96 hr respectively.

The resulting adjustment factor, K, is then used to project the initial t=0 data to t=96 theoretical by dividing the number of MNs at t=0 by K as in equation 2.

$$T96 = Mns\ 96\ hr\ theoretical = MNs\ 0\ hr/K \quad (2)$$

As shown in Table 1, K can vary considerably, based on the amount of blood obtained at t=0. However, by using this factor to project the t=0 number of MNs to t=96 hrs, it is possible to evaluate the change, $\Delta$, that have occurred in the micronucleated cell population by subtracting the theoretical number of MNs at t=96 hrs (T96) from the experimentally observed number of MNs at t=96 hrs (A96).

$$\Delta = A96 - T96 \quad (3)$$

where

A96 is the number of micronucleated cells counted in the 96 hour blood sample,

T96 is the projected (theoretical) number of MNs that should be present at 96 hours, $\Delta$ is the change in the number of MNs at 96 hours relative to the number at t=0.

In the case of control mice, one would expect to see only slight changes in the MN numbers which would parallel the spontaneous background increase due to new PCEs, or about two MNs/1000 PCEs. Each of the first five entries in Table 1 are control mice that were bleed at 0 and 96 hrs. Notice that the difference, $\Delta$, between A96 (i.e. MNs actual) and T96 (i.e. MNs theoretical) is very low as expected for all controls (Average 4±14 MNs/10,000 PCEs). The last five entries are mice that were bleed at t=0 and received an intraperitoneal injection of MMS (100 µg/g body weight) at t=0 and t=48 hours. A final blood sample was obtained at 96 hours. Again, a considerable variation in the K value was obtained due to bleeding. Normalization of the t=0 number of MNs again gives the t=96 MN theoretical (T96) as with the control mice. However, in this case, MMS exhibited clastogenic activity as shown by the increase in, $\Delta$ wherein an average of 329±28 MNs/10,000 PCEs wa obtained. Thus, both the low background activity of the controls and the elevated number of micronuclei in the clastogen treated mice are readily apparent using this process.

DUAL PARMETER ANALYSIS

Figure 6A:
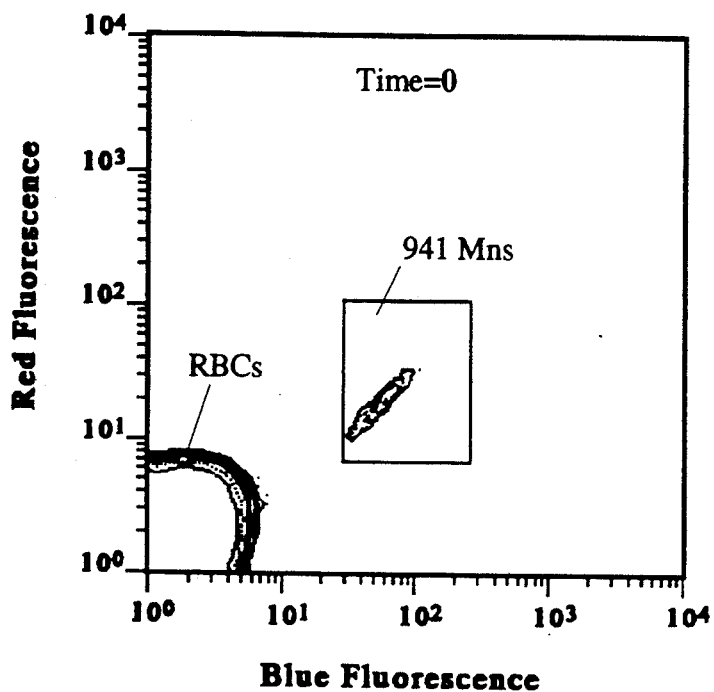
Figure 6B:
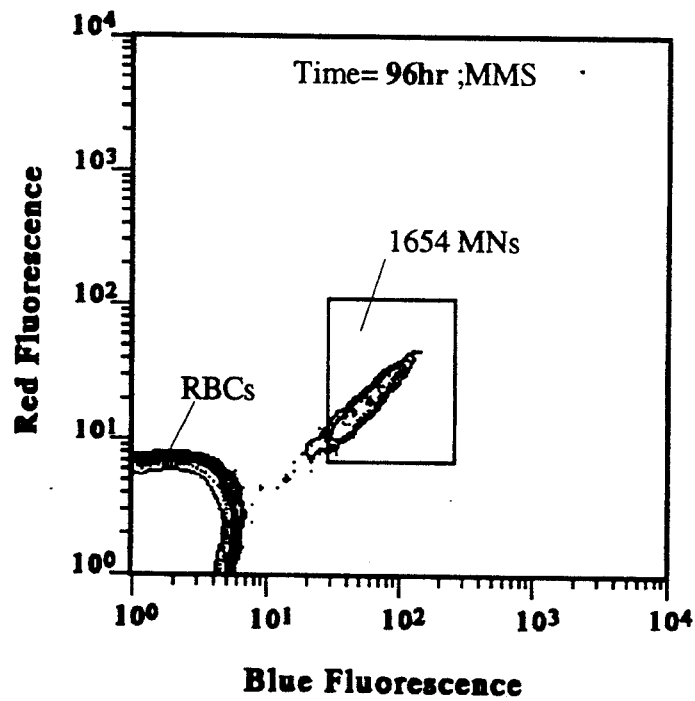

An alternative to list mode data acquisition is to obtain the data in a dual parameter mode. In contrast to list mode, where the fluorescence and light scatter properties of each cell are stored, dual parameter acquisition provides a running tally of the number of events of each type. As a consequence, it is not possible to reconstruct the experiment or reprocess the correlated data as can be done with list mode files where in it is possible to evaluate the properties of specific cells. An advantage of dual parameter acquisition is that it has relatively low data storage requirements. Thus, it is possible to store the dual parameter data from 1,000,000 cells in one tenth the disk space required to store 10,000 cells in list mode files. In those cases where large numbers of cells must be processed or where a complete overview of all cell populations is required, a dual parameter data acquisition format should be used. Accordingly, a second data processing embodiments of this invention is to acquire data in the dual parameter mode. To demonstrate this data acquisition method in conjunction with this invention, zero blood sample was obtained from a mouse which was then dosed with methylmethane sulfonate (MMS; 100 µgm/g body weight). In this case, the events were gated on cell size (forward light scatter), and the red fluorescence and blue fluorescence properties of each cell were acquired. FIG. 6A shows the pattern obtained for the zero hour blood sample that was fixed and stained with a single dye, Hoechst 33258, and 941 MN events were present in the analysis window. This analysis window was set by using the malaria parasite, *P. berghei*, as a guide as shown in FIG. 1A. FIG. 6B shows the pattern that resulted for the blood sample from a dosed with MMS at 0 and 48 hr and a final blood sample was obtained at 96 hours. In this case, 1654 MN events were present in the window (500,000 total cells were counted). The difference between the zero blood and the 96 hours blood (i.e. the change in Mn cells) was obtained using the analysis area shown in FIG. 6b and the results are shown in Table 3 for four control mice and four mice dosed with MMS. Blood samples from mouse #5 in Table 3 were used to generate the bivariate graphs that are shown in FIG. 6. Notice that the 96 hr sample has a more detailed contour pattern that the t=0 sample also indicative of the presence of increased numbers of MN-cells. By obtaining the zero blood for each mouse, it is possible to increase the sensitivity of the assay, and to observe clastogenic action with a single mouse while obtaining more data and better statistics than with conventional methods. With dual parameter analysis the change, $\Delta$, in the MN levels in the blood can be determined by a simple subtraction of the initial number of MNs at t=0 from the MNs at any later time (e.g. t=96 hr) as is shown in Table 3, and two facts are apparent.

TABLE 3

Analysis of Micronuclei in Blood from MMS treated and control mice per 500,000 cells (Dual Parameter Data; Cells stained with Hoechst 33258)

| Mouse Number | Treatment | Mns# (0 hr) | Mns# (96 hr) | $\Delta$ ($T_{96} - T_0$) |
|---|---|---|---|---|
| 1* | Saline | 969 | 967 | −2 |
| 2* | Saline | 859 | 922 | 63 |
| 3* | Saline | 906 | 924 | 18 |
| 4* | Saline | 839 | 896 | 57 |
| | | | mean = | 34 ± 31 |
| 5* | MMS | 941 | 1654 | 713 |
| 6* | MMS | 804 | 1424 | 620 |
| 7* | MMS | 848 | 1360 | 512 |
| 8* | MMS | 1122 | 1662 | 540 |
| | | | mean = | 596 ± 90 |

500,000 total erythrocytes were counted for each sample).
*Control mice received an IP injection of 0.9% saline.
*Mice received MMS (100 µg/g body weight; IP injection) at 0 and 48 hours.

First, the change (Δ) in MNs for the MMS dosed mice was significantly higher than the Δ values for the control mice in this case where 500,000 total cells were counted for each sample. Second, the change, Δ, highlights the clastogenic action of MMS, and the increase in MN-cells is evident even with a single dosed mouse. This pattern is consistent in the experiments described in this embodiment wherein the control mice gave consistently low (background) Δ values while the clastogen dosed mice exhibited elevated micronucleus levels as shown in the various Tables herein. In this example, a 96 hr assay window was defined by taking a final blood sample 96 hours after the initial sample (i.e. t=0) was obtained. With this invention, the analysis window can be expanded or contracted by timing the time interval between when the initial and final analysis samples are obtained.

Figure 7A:
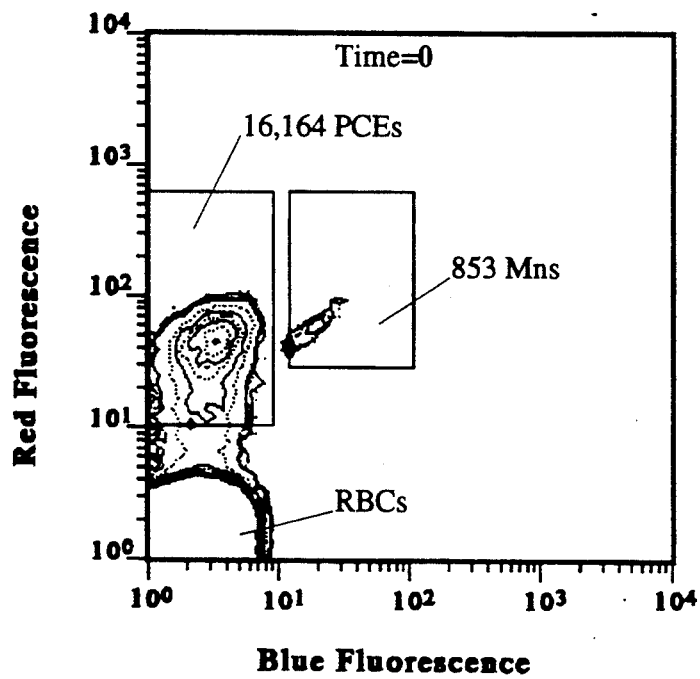
Figure 7B:
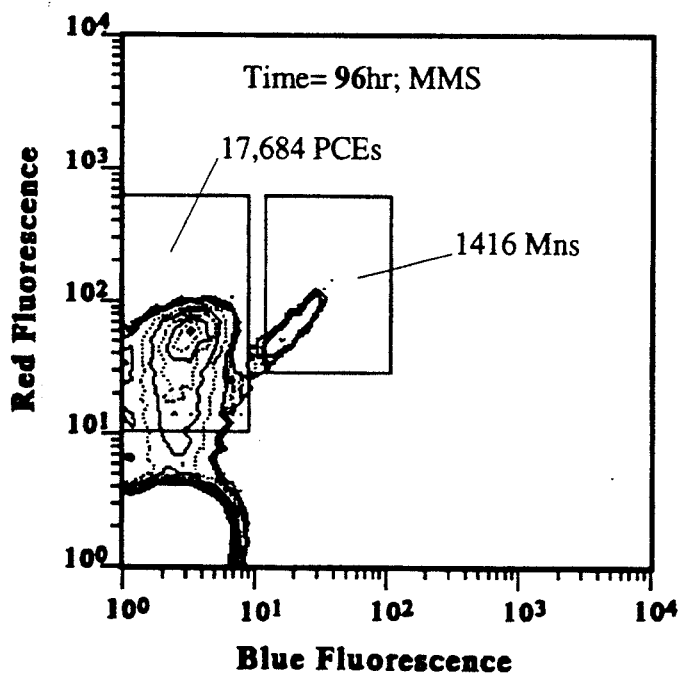

Another staining embodiment of this invention involves the use of dual parameter data acquisition in conjunction with two dyes, Hoechst 33258 and propidium iodide so as to analyze both MNs and PCEs. Simultaneous analysis of MNs and PCEs by flow cytometry has eluded practitioner in the art. Hoechst 33258 stains the DNA of the micronucleus whereas propidium iodide stains the RNA rich polychromatic cell population. With this dye combination, it is possible to obtain data reflecting the number PCEs and the number of MN-cells in a single experiment. FIG. 6 shows that when Hoechst 33258 is used alone, the PCEs are transparent and are located in the RBC contour at the origin. In contrast, FIG. 7 shows the effect of the two dyes on the resolution of the cell populations. Propidium iodide endows the PCEs with a strong red fluorescence signal which pulls them out of the RBC contour. At the same time, the variability in the RNA content of the PCE population results in a continuous contour pattern that extends to the RBC region of the bivariate graph. The MNs are still clearly resolved as they were in FIG. 6A with Hoechst 33258 stain alone, and an analysis area is shown for both PCEs and MNs. These areas were used to generate the data that is shown in Table 4. Blood samples from mouse #5 (Table 4) has been used to generate FIG. 7. The same analysis areas were used for the data from the other seven mice represented in this Table. The differences between dosed mice and control mice is clearly evident. (Control mice difference averaged 18 MN cells whereas the dosed mice averaged 535 MN-cells).

In addition to providing a clear reading on clastogenic action, this process also permits a quantitative analysis of changes in the PCE population. This is shown for Mouse 190 1 in Table 3 where the PCE levels increased from 16,033 at t=0 to 23,878 at t=96 hr. The occurrence of this bleeding related phenomena is also evident in FIG. 5 where increases in the PCE population are graphically shown. The observations that changes in the relative number of PCEs occur following bleeding, were used to normalize the list mode files as described for the data in Table 2. In other cases, we have observed decreases in the PCE population. Such is the case when mice are dosed with dimethyl benzathracene (DMBA), wherein the production of PCEs is suppressed. To further show this decrease in PCEs, note that the malaria blood that was stained with Hoechst 33258 and propidium iodide (FIG. 1B) is lacking the PCE contours. The on set of parasitemia results in a substantial suppression of PCE (and therefore RBC) formation. The long range repercussions of this suppression is severe anemia and eventually death to the mouse. Thus, this invention is able to monitor and measure changes that occur in the differentiation of blood cells as evidenced by the relative number of PCEs in a sample. The ability to rapidly and quantitatively analyze PCEs by this process provides a means for monitoring the effects of chemicals on stem cell differentiation. Although the nucleated cells have been gated out for this example, the data on the dynamics of nucleated cells could be easily included in the data base as will be shown later.

DATA PROCESSING BY SINGLE PARAMETER ANALYSIS

Figure 8:
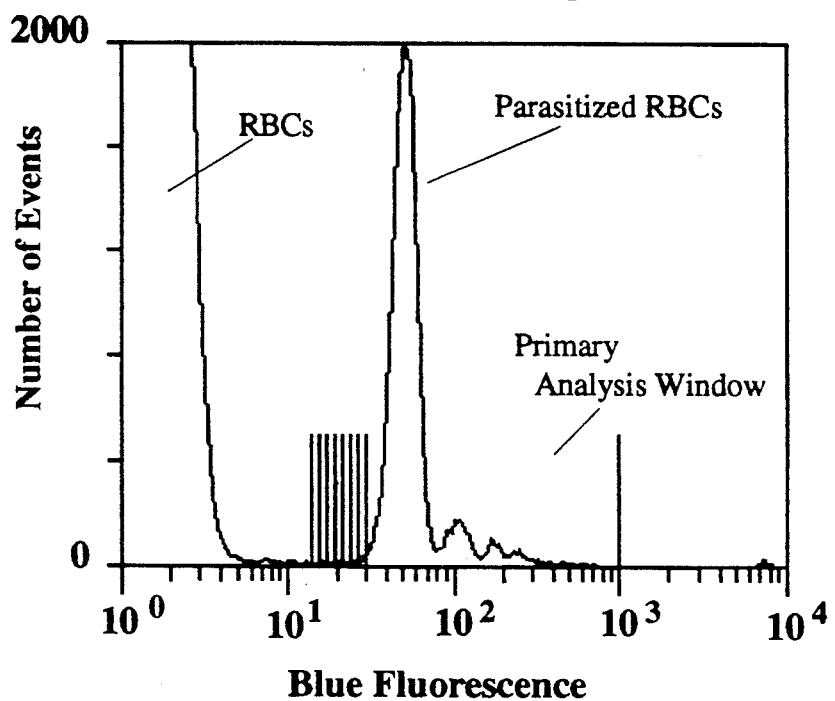

The resolution of the blue fluorescence signal as shown in FIG. 6 also suggests that the increase in Mn-cells could also be evident with single parameter analysis. In order to show this single parameter embodiment of this invention, the instrument was aligned with the malaria parasite, $P.\ berghei$, data was acquired, and analysis windows were defined relative to the malaria peak. FIG. 8 shows the single parameter histogram that was obtained for the malaria infected blood that was fixed and stained with Hoechst 33258. A prominent peak, characteristic of cells single parasites, is evident. The primary analysis window was used to bracket the main peak and extends to the third log has mark. In addition, seven smaller equally spaced secondary analysis areas are also shown in FIG. 8. The secondary areas are presented in order to demonstrate the effect that a small change in the position of the analysis window could

TABLE 4

Analysis of Micronuclei in Blood from MMS treated and control mice per 500,000 cells (Dual Parameter Data; Cells stained with Hoechst 33258 & Propidium Iodide)

| Mouse Number | Treatment | PCEs (0 hr) | PCEs (96 hr) | Mns# (0 hr) | Mns# (96 hr) | | ΔMns ($T_{96} - T_0$) |
|---|---|---|---|---|---|---|---|
| 1* | Saline | 16,033 | 23,878 | 841 | 904 | | 63 |
| 2* | Saline | 14,906 | 13,252 | 845 | 814 | | −31 |
| 3* | Saline | 14,963 | 16,120 | 904 | 917 | | 13 |
| 4* | Saline | 17,332 | 17,899 | 809 | 789 | | −20 |
| | | | | | | mean = | 6 ± 42 |
| 5˙ | MMS | 16,164 | 17,684 | 853 | 1416 | | 563 |
| 6˙ | MMS | 10,443 | 15,408 | 737 | 1394 | | 657 |
| 7˙ | MMS | 13,740 | 13,095 | 883 | 1282 | | 399 |
| 8˙ | MMS | 13,263 | 14,356 | 1015 | 1535 | | 520 |
| | | | | | | mean = | 535 ± 107 |

Figure 9A:
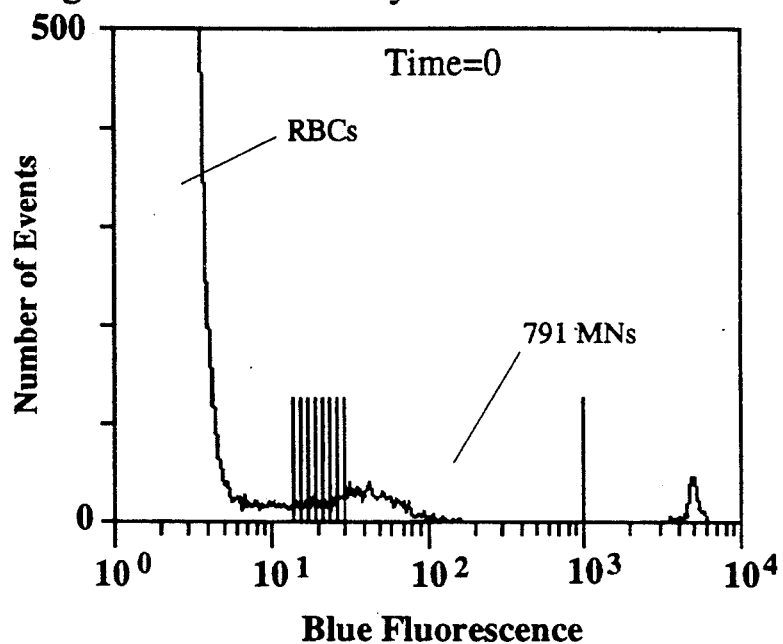
Figure 9B:
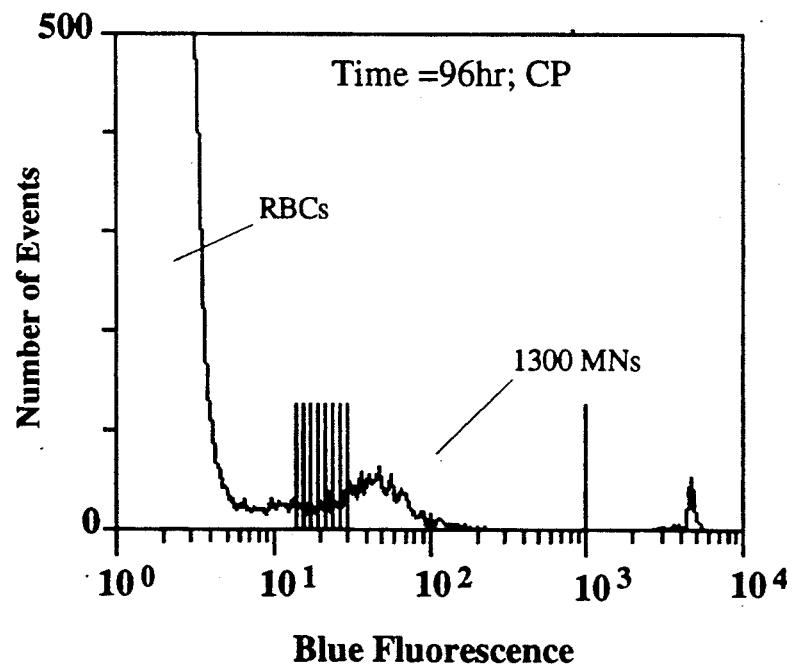

500,000 total erythrocytes were counted for each sample.
*Control mice received an IP injection of 0.9% saline.
˙Mice received MMS (100 μg/g body weight; IP injection) at 0 and 48 hours.

have on the Mn-cell count. Blood samples (t=0 and t=96 hr) from a mouse that was dosed with cyclophosphamide (at t=0 and t=48 hrs) were stained with Hoechst 3325k and the events were also acquired in the single parameter mode. FIGS. 9A and 9B show the blue fluorescence histograms that were obtained for the t=0 and the t=96 hr samples, respectively. The analysis windows shown in FIG. 9 are those that were initially set up with the malaria infected blood sample shown in FIG. 8. The number of events present in the primary analysis windows are shown. Table 5 provides a listing of the number of MN-cell events that are present in each of the eight windows, beginning with the larger primary window and then moving to the left sequentially. By adding each consecutive window to the primary, it becomes evident that the step wise expansion of the window increases the number of MN-events. The sum0 and Sum96 column entries show the increase in Mn events at each expansion step. The last column gives the difference, $\Delta$, between the t=0 control and the t=96 hr sample at each interval and shows that the number of micronucleus events increases as each step function is added to the primary window area. This observation is not surprising in view of the contour patterns shown in FIGS. 6 and 7 where the 96 hr pattern is extending outside the analysis area. In any case, the clastogen stimulated increase in MNs is clearly evident using the primary window, based on the *P. berghei* pattern, or with any of the expanded window configurations. This result shows that considerable latitude exists for setting the blue fluorescence analysis window, assuming that the integrity of the patterns is not compromised by instrument changes. Consider the case of instrument drift in which a slight decrease in signal level occurs.

stream stability, signal output, etc. during many hours of analysis? Any inadvertant shifting from the initial tuned position could adversely affect the quality of the data that is acquired. The histograms shown in FIG. 9 and the data in Table 5 suggest that the position and size of the analysis window will influence the actual number of events for each sample. The difference, $\Delta$, between the t=96hr and t=0 hr samples further suggests that a greater increase in MN-events can be obtained by expanding the analysis window. Whereas the difference, $\Delta$, was 509 for the primary analysis window, the addition of all seven secondary windows gave a difference of 621 events. Thus, some flexibility exists in the actual positioning of the analysis window. However, the comparison of samples is predicated on the assumption that the fidelity of data acquisition is maintained for each sample that is run. If instrument drifting occurs, such that some of the cells of interest slip out of the analysis window, the number of events will be inaccurate and lower than the true value. For example, if an analysis slice the size of the secondary windows in Table 5 drifted to the left (i.e. out of the primary window as shown), a decrease of about 100-150 events could occur in this selected analysis area. Similarly, if events present in the nearest secondary window drifted upward into the primary window, the number of events acquired would be higher by 70-90 or more depending upon the magnitude of the shift. In order to minimize instrument drift, a method was needed to check alignment before each sample was run. As indicated earlier, neither RBC, PCEs, MN-cells nor the nucleated cell populations provide proper signals for evaluating instrument alignment since they are either nor present in sufficient quantities, the populations are too dispersed, or cell staining variations would be introduced. Ac-

TABLE 5

The Effect of the Analysis Window Size on The Change in Micronucleous Events

| Analysis Window | Window* Location | (t = 0 hr) | | (t = 96 hr) | | ($t_{96} - t_0$) |
|---|---|---|---|---|---|---|
| | | Events in Window | $Sum_0$* | Events in Window | $Sum_{96}$* | Difference ($\Delta$) |
| 1 | Primary | 791 | — | 1360 | — | 569 |
| 2 | Right-most | 71 | 862 | 90 | 1480 | 618 |
| 3 | | 61 | 923 | 83 | 1563 | 640 |
| 4 | (secondary | 59 | 982 | 81 | 1644 | 662 |
| 5 | windows) | 55 | 1037 | 69 | 1713 | 676 |
| 6 | | 66 | 1103 | 65 | 1778 | 675 |
| 7 | | 50 | 1153 | 61 | 1839 | 686 |
| 8 | Left-most | 51 | 1204 | 76 | 1915 | 711 |

*The large (primary) window is enlarged by adding on channel proceeding from the left edge of the primary window to the left-most secondary channel as shown in FIG. 9.
*The $Sum_0$ and $Sum_{96}$ value in each case shows the increase in events that is obtained by the sequential addition of adjacent windows to the primary window for the t = 0 hr and the t = 96 hr samples, respectively.
The increase in MN events is given by obtaining the difference, $Sum_{96} - Sum_0$ for each incrementally expanded window.

The results in Table 5 suggest that a drift of even a few channels can increase or decrease the number of events in the window by 40-100 counts, and thus, could impact unfavorably on the MN analysis. Instrument stability is, thus, a key ingredient in the execution of this process.

QUALITY CONTROL DURING DATA ACQUISITION

Practioners in the art are presently unaware of the need for internal quality control on the flow cytometer signals during the analysis of each sample. A typical micronucleus test could involve the analysis of 40 to 100 samples over the course of a day. Is it fair to assume that the flow cytometer will remain stable in laser power, cordingly, a reasonable alternative was to introduce microspheres into each samples that would be used solely as an internal instrument quality control check on each sample before and during acquisition.

Figure 10:
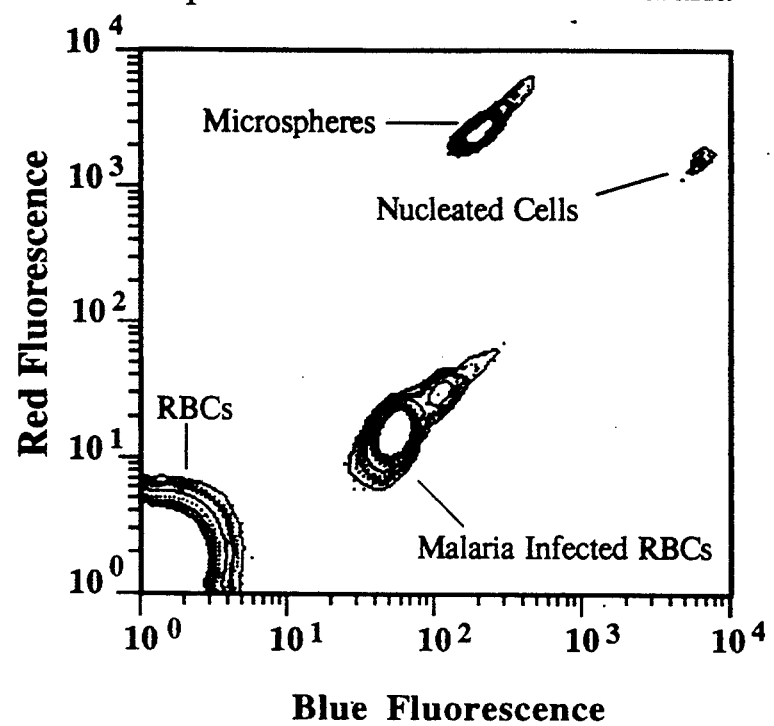
Figure 11:
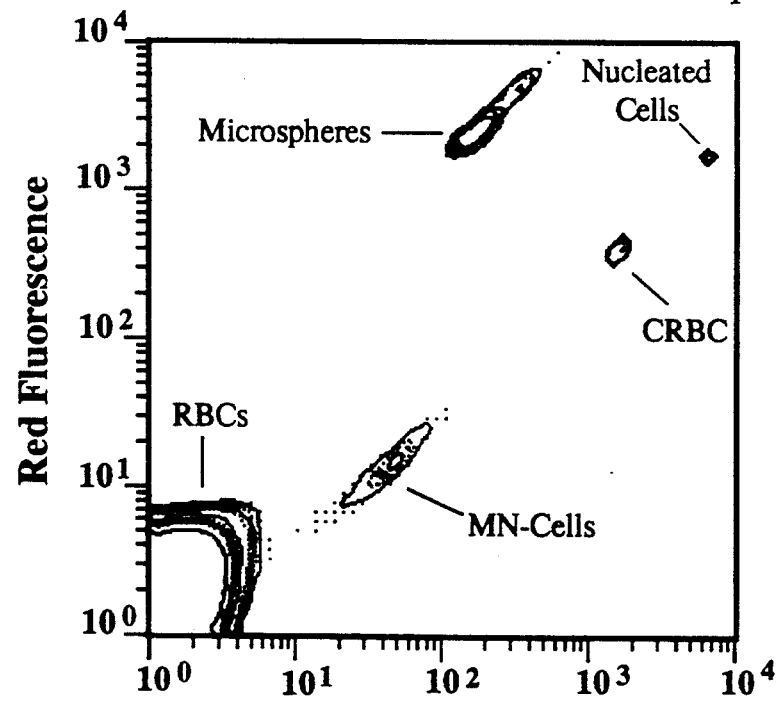
Figure 12:
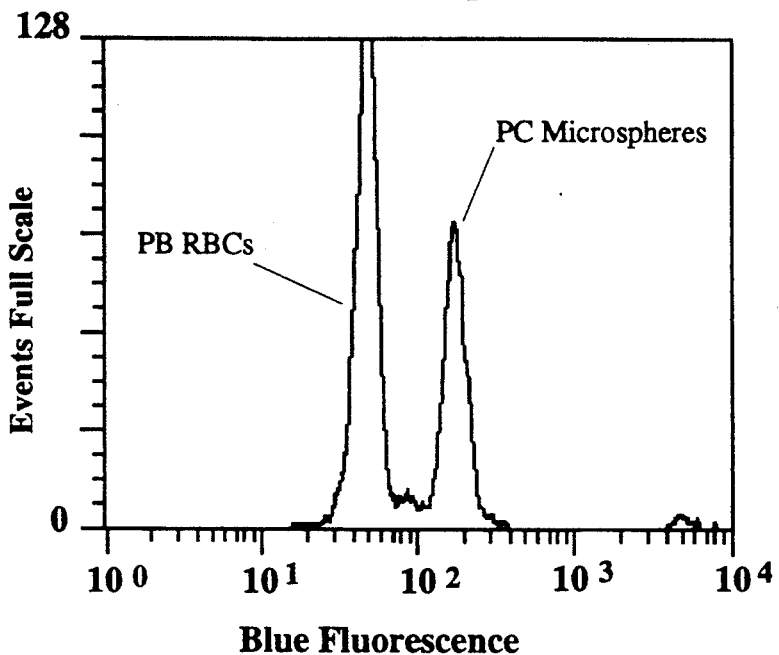
Figure 13:
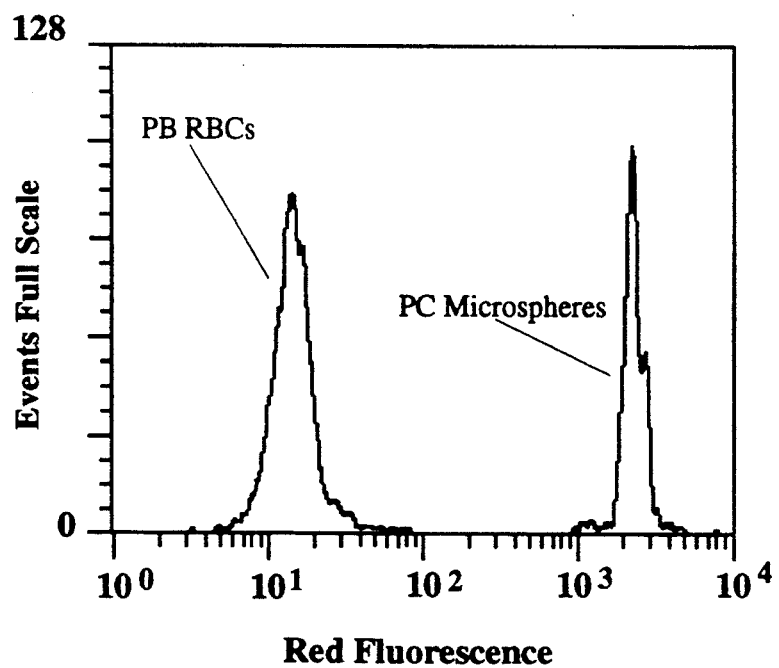

In this embodiment of the invention, I have used polychromatic (PC) microspheres (6 μm; Polyscience Corp), which give a strong red signal when excited with a 363 nm wavelength laser beam. When these microspheres were introduced into a *P. berghei* infected blood sample that had been stained with Hoechst 33258, a bivariate pattern shown in FIG. 10 was obtained. Notice that the microspheres are located in the upper quadrants of the pattern and can thus be gated out by imposing a red gate above the parasite position when actual data acquisition begins. Since these microspheres are permanently fluorescent, they are not subject to staining variation that might occur in the cell populations. As a consequence, they provide a sensitive indication of changes in alignment that occur over the course of a multi-sample analysis. A further example showing the distribution of three controls in a micronucleus sample is provided in FIG. 12. As in the preceding malaria sample, PC-microspheres are included in this sample for monitoring instrument drift. In addition, chick red blood cells (CRBCs) were also added. It is known to practioners in the art that avian blood cells contain a nucleus with somewhat less DNA than the nucleus of the mouse cells. As with parasitized blood, the use of microspheres and/or CRBCs to optimize cell fixing, cell staining, and a flow cytometry based micronucleus assay have not been known to practioners. Note that the CRBCs exhibit a very tight contour pattern that is located between the micronucleated cells (i.e. MN-Cells) and the nucleated cells. The nucleated cells are an internal standard that can also be used to monitor changes in conditions that would impact on data acquisition. This figure further shows where the micronucleated cells fit in the dynamic range of these cell systems. At the lower end of the dynamic range are the RBCs which do not contain DNA. At the upper end of the range are the nucleated cells. Both MN-cells and CRBCs fit nicely between these two extremes as would be expected. It is interesting that the CRBCs contour falls on a line connecting the MN-cells and the nucleated cells. In using the microspheres, CRBCs or naturally occuring nucleated cells for monitoring purposes both the shape of the contour or dot pattern and the position of the peak can highlight a problem situation. We have observed situations wherein an elongation of the contour occurs due to insuffient dye loading. By allowing a 5–10 minute incubation interval, the contour pattern shown in FIGS. 10 and 11 can be achieved. Although the bivariate graphs show the overall distribution of the microspheres and cell standards, and the position (e.g. the third log line) where a red gate should be introduced to gate out said standards, I have found that single parameter histograms provide a more sensitive pattern for the routine adjustment for instrument drift. Operationally, the PC-microspheres (1 μl PC-microsphere/2 ml cell sample) are first added to the fixed and stained malaria blood sample. As usual, the cytometer is aligned to provide a good parasite signal in the region as shown in FIG. 10 and FIG. 2, providng an overview of the components in the sample. Good resolution is achieved between the microspheres and the different cell populations in this bivariate profile. The peak of the malaria contour displayed in FIG. 10, is positioned on histogram as shown in FIG. 12 and FIG. 13. RBCs have been gated out of these histograms so as to focus on parasite and microsphere events. Increase or decrease in the photomultiplier gains are used to position said malaria cells as shown in the red and blue fluorescence histograms. The position of the peak of the microsphere pattern is determined by superimposing a gate marker over the highest dot. If acquisition is then restarted, the highest dot should move along the gate marker and is evident as a black segment on the white marker line. Conversely, if the instrument has drifted, the peak dot will be seen to the right or left of the marker line and an adjustment in gains (or in some cases, back-flushing the nozzle) may be necessary to realign the sample. FIGS. 12 and 13 shown the malaria and microsphere alignment pattern for the blue fluorescence and red fluorescence histograms, respectively. Once this alignment is accomplished, the position of the microsphere peak is recorded, and location of said peak in the actual sample histograms is checked to insure that the instrument stability is maintained. PC-microspheres are added either to the dye-buffer stock solution or to individual samples of stained cells. The absolute quantity is not critical since they can be gated out, and therefore need not be present during acquisition. In contrast to the malaria infected blood sample shown in FIGS. 12 and 13, uninfected blood, when run under these conditions, will show a single microsphere peak which will highlight any instrument drift. I have further observed that alignment of the blue fluorescence signal may be m ore crucial than the red signal in checking for instrument drift. By calibrating the microspheres versus the malaria parasite peak, and also setting the analysis window to encompass the parasite peak, the analysis of unknown samples with low levels of MN-events can be effectively retained in the window.

The quality control procedure outlined herein used PC-microspheres and the Hoechst 33258 stained cells as an example of this embodiment. Other microspheres could be used having different sizes or different fluorescent properties, providng that they could reflect the stability or drifting of the instrument for each sample. Fluorescence was used as an example for routinely evaluating instrument alignment. It is feasible to use forward light scatter and side scatter to evaluate instrument stability. Once instrument fidelity is checked, the microsphere should be gated out so as not to added irrelevant events to the total cell count during actual acquisition. With PC-microspheres present, an upper red gate can be set (such as that shown in FIG. 13) and only events below the gate will be acquired. Only the position of the microspheres on the blue fluorescence histogram needs to be routinely checked and adjusted prior to data acquistion. Alternatively, the microspheres could be included in the acquisiton, and could be gated out during the analysis phase.

DEMONSTRATION OF THE PROCESS WITH A SECOND CLASTOGEN-CYCLOPHOSPHAMIDE

A final embodiment of this invention involves the application of the process to evaluate the clastogenic activity of another chemical agent. Since the clastogenic activity of cyclophosphamide has been documented, it was chosen as a another example of this embodiment. In this case, the mice were bleed at t=0 and received a dose of cyclophosphamide (100 μg/g body wt) at 0 and 48 hours. A final blood sample was obtained at 96 hours, whereupon the samples were fixed and stained with Hoechst 33258. The samples were analyzed in the dual parameter mode wherein 1,000,000 total events were acquired for each sample. Table 6 shows the results that were obtained for this experiment. As with the MMS experiments, a large increase in MN formation was observed in the dosed mice. To further show the flexibility of this method, the data were processed in three different ways as shown in Table 6. In the first method, a difference was obtained between the t=0 and the t=96hr values for each mouse and resulted in a unique change ($\Delta$) that is specific for each mouse as shown in the last column. The data for the saline controls and the cyclophosphamide mice were averaged and gave mean values of 77 and 1124 MN-cells, respectively. The difference of the mean values shows a 1047 increase by this method. In a second approach, the data from individual sets of mice can be sumed as shown in Table 6, and the difference between the resulting t=96hr and t=0 means can be determined for control (76 events) and dosed (1123 events) mice. The difference between the mean values yielded a 1047 increase in MN-cells. Finally, it is possible to ignore the t=0 values and compare the means of the t=96 hr samples (1602 controls; 2954 dosed), whereupon the difference gives an increase in 992 MN-cells. All three methods clearly show the increase in MN-cells in the cyclophospamide dosed mice.

ability that a chromosome break will occur is significantly increased. Practioners in the art are unaware of this increase in sensitivity due to initial bleeding. To demonstrate the increased sensitivity of this invention, an experiment was designed to evaluate the effect of the same treatment with MMS in conjunction with three different bleeding schedules. In this experiment, control mice were dosed with 0.9% saline, whereas treated mice received MMS (100 μg/g body wt.) at 0 hr and at 48 hrs. The first set of mice (the L series) were not bleed prior to obtaining a 96 hour blood sample. The MN-cell level resulting from MMS treatment would reflect the

TABLE 6

Analysis of Micronuclei in Blood from Cyclophosphamide treated and control mice per $10^6$ cells (Dual Parameter Data; Cells stained with Hoechst 33258)

| Mouse Number | Treatment | Mns# (T = 0 hr) | Mns# (T = 96 hr) | Difference $\overline{Mn_{96}} - \overline{Mn_0}$ | Δ ($T_{96} - T_0$) |
|---|---|---|---|---|---|
| 1* | Saline | 1432 | 1542 | | 110 |
| 2* | Saline | 1576 | 1732 | | 156 |
| 3* | Saline | 1527 | 1569 | | 42 |
| 4* | Saline | 1569 | 1567 | | −2 |
| Mean | | 1526 ± 66 | 1602 ± 87 | (76) | 77 ± 70 |
| 5° | CP | 1492 | 2591 | | 1099 |
| 6° | CP | 1414 | 2453 | | 1039 |
| 7° | CP | 1552 | 2626 | | 1074 |
| 8° | CP | 1426 | 2708 | | 1282 |
| Mean | | 1471 ± 64 | 2594 ± 106 | (1123) | 1124 ± 108 |
| Increase in MNs (Mean$_{CP}$ − Mean$_{Saline}$) | | | | (1047) | 1047 |

1,000,000 total erythrocytes were counted for each sample.
*Control mice received an IP injection of 0.9% saline.
°Mice received cyclophosphamide (CP) (100 μg/g body wt.; IP injection) at 0 and 48 hours.

INCREASED SENSITIVITY DUE TO BLEEDING

Earlier, it was pointed out that obtaining an initial blood sample (t=0) provides an important background measurement of the number of micronucleii in each mouse. Obtaining an initial blood sample also increases the sensitivity of the assay, due to the stimulation of the stem cells to replenish the lost blood. Clastogen action should be increased if cells are actively turning over, rather than subsisting in a quiscent state. In the absence of bleeding, new PCEs are introduced into the blood cells at a low steady state level and MNs are introduced at a spontaneous background level. If cells are actively turning over during clastogen treatment, then the probability of clastogen action in the steady state stem cell turnover rate. The second set of mice (the M series) were bleed 166 hrs prior to the initial clastogen dose. In this set, the minus 166 hr bleeding will cause stem cell proliferation and differentiation, but the system should begin to return to steady state once the blood is replenished. The third set (the K series) was bleed at t=0hr where upon dosing was initiated, and a final blood sample was obtained at t=96 hrs. Table 7 shows the results of this experiment.

TABLE 7

The Effects of Bleeding on The Sensitivity of the Micronucleus Assay*

| Mouse Number | Bleeding Schedule | Treatment Saline (C)° | Treatment MMS(D)° | Increase in MNs (D − C) |
|---|---|---|---|---|
| L Series | | | | |
| 1 | Initial blood - no | 1025 | 1352 | |
| 2 | Final - 96 hrs | 1020 | 1390 | |
| 3 | | 1084 | 1331 | |
| Mean | | 1043 ± 36 | 1357 ± 30 | 314 |
| M Series | | | | |
| 1 | Intial - (−166 hr) | 1218 | 1776 | |
| 2 | Final - 96 hr | 1171 | 1541 | |
| 3 | . | 1061 | 1673 | |
| Mean | | 1150 ± 81 | 1663 ± 118 | 513 |
| K Series | | | | |
| 1 | Initial - at t = 0 | 1097 | 1829 | |
| 2 | Final - 96 hr | 974 | 1794 | |
| Average | | 1035 | 1812 | 777 |

*Three different bleeding protocols were followed as described in the text in order to evaluate the effect of the initial bleeding on the assay sensitivity. Only 96 hour samples were analyzed for micronucleii and the difference between the means of the treated and control samples is given in the last column.
°Control mice were dosed with 0.9% Saline at t = 0; treated mice received 100 μg MMS/g body wt. Two doses were given in each case at 0 hr and 48 hrs, and a final blood sample was obtained at 96 hrs.

Since the L series was not initially bleed, the initial blood samples were not used in the analysis of the M or K series for equal comparison with L. Rather, only the 96 hour blood samples were analyzed in each set. The difference, D, between the saline controls and the dosed mice should reflect the level of turnover of the stem cells and the suseptibility of said cells to clastogen action in each case. The results indicate that the L-mice, which were not bleed gave the lowest number of micronucleated cells (i.e. 314 above background). Although the M series had 166 hrs to recover from the initial bleeding before being dosed with MMS, the stem cells still appear to be fairly active, and an intermediate level of micronucleated cells was obtained (i.e. 513 events above background). Finally, the highest activity was obtained with the K-series wherein the mice were bleed and immediately dosed. In this case, the stem cells are turning over at a high rate to replenish the blood at a time when the concentration of MMS is also high. As a consequence, the K-mice displayed a large increase in the number of micronucleated cells (777 events above background). These results suggest therefore, that the sensitivity of the micronulceus assay is significantly increased by obtaining an initial blood sample immediately before dosing begins so as to provide the highest concentration of test agent during the period of most rapid stem cell turnover. The results in Tables 2 and 4 provide additional experimental evidence that bleeding stimulates stem cell proliferation and differentiation. Specifically, these Tables show that the PCEs increased significantly by 96hrs for different mice, as the mouse begins to replenish the lost blood. This increase in sensitivity could be particularly important in cases where a week clastogen is being investigated.

CYCLOPHOSHAMIDE DOSE RESPONSE EXAMPLE

Figure 14:
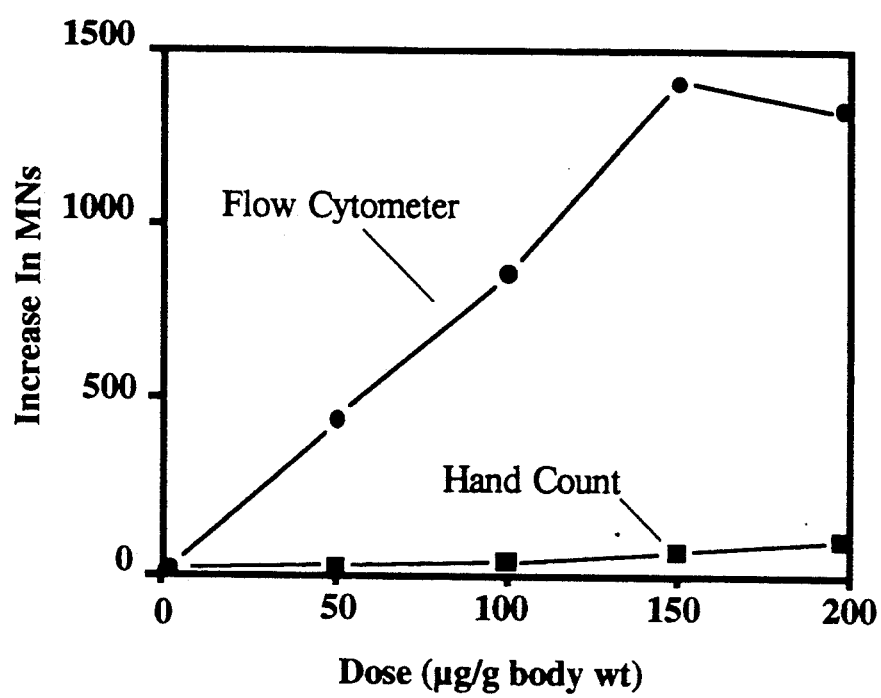

Preceding examples of this invention showed the comparison of control blood (i.e. from mice dosed with saline) and blood from mice dosed with an elevated level of a clastogen (either MMS or CP). However, an effective flow cytometry based micronulceus assay should also be able to reflect changes in the number of MN-cells at different doses of a clastogen. Accordingly, another example of this embodiment involves a cyclophosphamide dose response analysis. Ten mice were divided into sets of two for this experiment. An initial blood sample was taken (t=0hr) for each mouse. The two control mice were dosed with saline while the other sets received different doses of cyclophosphamide (50,100,150 or 200 µg/g body weight). Each set was treated twice, at t=0 and t=48 hrs. Final blood samples were obtained at t=96hrs, and were fixed and stained with Hoechst 33258 to which PC microspheres had been added. The position of the microsphere peak was initially calibrated using the malaria infected RBCs as the primary standard. Each sample was then checked to insure that the microsphere peak was still at the calibrated position before acquisition. Some slight adjustments were necessary in the gains during the course of the analysis, during which ten t=0 samples and ten t=96 samples were run. One million total cells were counted for each sample. Gates were set on forward scatter (e.g. FIG. 3), side scatter (before the major cell peak), and a red gate (e.g. as shown in FIG. 13). These gates insured that only red blood cells and their associated micronuclei would be acquired. Following acquisition, the number of micronucleated cells at t=0 were subtracted from the number at t=96hr for each mouse. Duplicate samples were averaged, and the average number of MNs was plotted as a function of the dose as shown in FIG. 14. The average for the saline controls were slightly negative, and were recorded as zero in this graph. A dose response relationship is evident in this Figure. In addition, the high doses were approaching 1500 events more than the zero (control) values. This example further shows the high sensitivity that is obtained by initially bleeding the mice to stimulate stem cell turnover followed by the analysis of the change between the zero and 96 hours samples. For comparison, the 96hr samples were also hand counted and the number of MNs/1000 PCEs were determined. The lower entries in the graph shows the low sensitivity obtained in the hand counted samples.

REPRODUCIBILITY OF THE ANALYSIS

Using the assay conditions as defined herein, the process defined in this embodiment will give much better reproducibility than the conventional manual assay. The statistics of the assay are significantly improved, due to the large number of cells that are routinely processed with this process. As discussed earlier, the manual scoring procedure determines the number of MNs per 1000 PCEs, and a large counting error of about 100% is common for the control samples (e.g. $2\pm2$ MNs/1000 PCEs). This large error is in sharp contrast to the small experimental error that is obtained by flow cytometry. Table 8 shows the reproducibility that is obtained when the same samples are run multiple times. In order to provide a suitable control for evaluating the deviation of the MN-cells, unstained samples of blood were doped with red PC-microspheres at a high and low density, thus bracketing the number of MNs in the stained sample. Samples were taken from this stock solution and were run six separate times, and gave the results shown in the high and low microsphere columns respectively. For comparison, a stock solution of a fixed blood sample containing a high number of MN-cells was stained with Hoechst 33258 and eight separate samples from the stock solution were run through the flow cytometer (363 nm wavelength; 84 mW) as described herein. The mean values were calculated for each set. The first sample set with a low microsphere content gave a mean of 1020 microspheres±20 or a 1.96% deviation. The higher microsphere sample gave a mean of 4897 microspheres ±42 or a 0.86% variation. This microsphere data provides a basis for comparison of the micronucleus data shown in the last column. For the micronulceus analysis, a mean value for the eight runs was 3977 MNs ±61 or a 1.54% deviation. Thus, the reproducibility of the described process in analyzing MNs is very high.

TABLE 8

| | Reproducibility of the Analysis When the Same Sample is Run Multiple Times* | | |
|---|---|---|---|
| Run | Low Microsperes≠ with Blood Cells | High Microspheres≠ with Blood Cells | Micronucleated* Cells |
| 1 | 1002 | 4884 | 3993 |
| 2 | 1030 | 4968 | 3886 |
| 3 | 1053 | 4884 | 4013 |

TABLE 8-continued

| | Reproducibility of the Analysis When the Same Sample is Run Multiple Times* | | |
|---|---|---|---|
| Run | Low Microsperes≠ with Blood Cells | High Microspheres≠ with Blood Cells | Micronucleated° Cells |
| 4 | 1003 | 4909 | 4010 |
| 5 | 1007 | 4896 | 4047 |
| 6 | 1023 | 4840 | 3885 |
| 7 | — | — | 3961 |
| 8 | — | — | 4019 |
| Mean | 1020 ± 20 | 4897 ± 42 | 3977 ± 61 |
| % variation | 1020 ± 1.96% | 4897 ± 0.86% | 3977 ± 1.54% |

*Stock solutions of the three different cell preparations were prepared and individual samples were removed and were analyzed as separate samples to evaluate the reproducibility of the analysis for microspheres and for stained cells. One million total cells were analyzed in each case.
≠An unstained fixed blood cell preparation was used to prepare a stock solution to which microspheres were added, and the sample was diluted further with blood to obtain a high and a low microsphere level. Six separate samples of the stock solution were then analyzed.
°A stock solution was prepared with sample having an elevated MN level. The cells were stained with Hoechst 33258 and the number of MN-cells was determined for eight separate samples from the stock solution.

With this process it is possible to obtain good quantitative data in those cases where clastogen action is weak or the dose of clastogen is low- even when the elevation in the number of MNs above the background level is slight. FIG. 14 showed that a good dose response relationship is obtained and the data at the lower doses clearly supports the conclusion that clastogenic action was present in this sample. In those cases where the increase is slight, it is possible to process more cells to further improve the analysis. The MN sample in Table 8 shows the type of data that can be obtained if 8,000,000 cells are analyzed. With this invention, it is now possible to support the conclusion of a clastogenic response with sufficient quality data.

The above detailed description and examples are intended for purposes of illustrating the invention and are not to be construed as limiting. The invention can be embodied otherwise without departing from the principles thereof, and such other embodiments are meant to come within the scope of the present invention as defined by the appended claims.

What is claimed is:

1. A flow cytometry process for determining changes, caused by chemical or biological agents, in blood or bone marrow cell populations selected from the group consisting of red blood cells, polychromatic cells, nucleated cells and micronucleated cells, comprising the steps of:
   a) sensitizing mice to said agents by initially bleeding them so as to increase the proliferation and differentiation of their blood stem cells, whereupon said sensitized mice are more susceptible to chromosomal damage;
   b) dosing the sensitized mice defined in step a) with a chemical or biological test substance so as to assess any resulting changes in proliferation, differentiation or clastogenic response of said cell populations;
   c) sampling blood or bone marrow cells of the mice defined in step b) at a prescribed time following dosing so as to obtain samples for analysis by flow cytometry;
   d) fixing the blood or bone marrow cells defined in step a) and step c) with an organic fixative at ultra low temperatures of less than −30° C. so as to cause said cells to exhibit both permeability to fluorescent dyes, and compatibility with flow cytometry analysis;
   e) staining nucleic acids of said fixed cells with fluorescent dyes in a concentration range that is compatible with flow cytometry analysis in order to highlight the DNA of nucleated cells and in some cases, the RNA of polychromatic cells;
   f) exciting the dye associated with the nucleic acids of the cells defined in step e) with a focused light beam of appropriate wavelength to produce fluorescent emission;
   g) monitoring the cell staining quality of said dyes by analyzing the fluorescence properties of a biological standard comprising fixed and stained parasitized cells, nucleated blood cells, or a combination thereof;
   h) calibrating photomultiplier tubes, contained within a flow cytometer to be used for analysis, with microspheres and with a biological standard to compensate for variations in staining, variations in the characteristics of the laser beam that forms part of said cytometer, and variations due to the type of cytometer used for analysis;
   i) monitoring flow cytometer instrument drift during each run by checking the location of the microspheres or nucleated blood cells that are either run separately or are included in each sample;
   j) tabulating the relative number of specific cell populations in said fixed and stained blood or bone marrow cells, by acquiring unique light scatter and fluorescent signals from said cells with detectors contained within said flow cytometer;
   k) analyzing the relative changes in the cell populations of step j), as between the cells originating from the initial bleed, and cells originating from the sampling after dosing, wherein the data is acquired in a form selected from the group consisting of list mode, dual parameter, or single parameter files.

2. The process of claim 1, wherein the sensitizing procedure defined in step a) is a means for stimulating stem cell proliferation, and obtaining an initial blood sample as a mouse specific background sample for comparison with a final blood sample from said mouse following treatment with a test substance.

3. The sensitizing process as defined in claim 1, step a), wherein the initial blood sample is obtained from one to ten days prior to the first dose of test substance administered at time=0 hour.

4. The process of claim 1, wherein the dosing procedure as defined in step b) comprises administering a single dose of the test substance at time=0 hour.

5. The process of claim 1, wherein the dosing procedure as defined in step b) comprises administering a dose of the test substance at regular intervals ranging from 24 to 48 hours, beginning at time=0 hour and ending at a later time when a sample is taken for analysis.

6. The process of claim 1, wherein the dosing procedure as defined in step b) comprises administering a dose of a test substance at time=0 hour, and administering a second dose at a later time.

7. The process of claim 1 wherein the sampling process as defined in step c) comprises obtaining a plurality of blood samples from each mouse so as to highlight different endpoints of proliferation, differentiation, and clastogenic action.

8. The process of claim 1 wherein the sampling process as defined in step c) comprises obtaining a final blood or bone marrow sample at a later time within the range of 24–144 hours following the initial dose of test substance.

9. The process of claim 1 wherein an initial blood sample is obtained from 1 to 10 days before injection of the test substance, followed by administration of one or more dose of test substance, and then obtaining a final blood or bone marrow sample at a later time within the range of 24–144 hours following the initial dose of test substance.

10. The process of claim 1 wherein an initial blood sample is obtained, followed by initiation of a subchronic longer term dosing regimen, and a final blood or bone marrow sample is obtained at the end of the study ranging from days to weeks following the initial dose of test substance.

11. The process of claim 1 wherein the fixing of cells as defined in step d) comprising:
  a) diluting from 5 $\mu$l to 500 $\mu$l of said cells with 5 ml to 100 ml of a solution of from 0.1% to 10% bovine serum albumin in phosphate buffered saline;
  b) centrifuging the diluted cells to separate them from other serum components to yield a cell pellet;
  c) fixing the pelleted cells with a volume of fixative agent selected from the group consisting essentially of methanol, acetone, and methanol-acetone solutions, wherein said fixing takes place at an ultralow temperature within the range from $-30°$ C. to $-90°$ C. for a time ranging from one to sixty minutes.

12. The process of claim 11, wherein the volume of fixative agent used, for fixing said cells is in the range from 0.1 to 20 milliliters.

13. The process of claim 11, wherein 15 $\mu$l of said cell pellet is suspended in 2 ml of methanol that was previously cooled to $-70°$ C., followed by incubation for 5 minutes at $-70°$ C.

14. The process of claim 11, wherein upon removal from ultralow temperature, said cells are diluted with 5 to 10 volumes of 1% bovine serum albumin in phosphate buffered saline, and are thereafter subjected to centrifugation to yield a fixed cell pellet that is suitable for long term storage at $0°$ C.

15. The staining process as defined in claim 1, step e), wherein the fluorescent dyes used for staining said cells are selected from the group consisting essentially of ethidium bromide, propidium iodide, acridine orange, DAPI, Hoechst 33258, and Hoechst 33342, or a combination thereof.

16. The process of claim 15, wherein the fluorescent dye used for staining said cells is Hoechst 33258 within a concentration ranging from 0.1 $\mu$g/ml to 1 mg/ml.

17. The process of claim 15, wherein said cells are treated with a stain specific for DNA, and a stain specific for RNA, and said stains are applied within a concentration ranging from 0.1 $\mu$g/ml to 1 mg/ml, and in a temperature range from $4°$ to $40°$ C.

18. The process of claim 17, wherein the stain specific for DNA is Hoechst 33258, and the stain specific for RNA is propidium iodide.

19. The excitation process as defined in claim 1 step f), wherein chromophores of said dye associated with the nucleic acids of the cells are excited with a focused ultraviolet or visible light source to produce distinct fluorescent emissions, said cells selected from the group consisting of micronucleated cells, nucleated cells, and polychromatic cells, or a combination thereof.

20. The process of claim 19, wherein said light source comprises a single laser beam.

21. The process of claim 19, wherein said light source comprises beams from two lasers at different wavelengths which are directed to interrogate cells at two distinct points along a sample stream thereof, and with each beam exciting one or more complementary chromophores in said cells.

22. The process of claim 19, wherein said light source comprises a focused beam from a high pressure mercury lamp.

23. The monitoring process as defined in claim 1, step g, wherein the fluorescence and light scatter properties of biological standards are employed to calibrate the fluorescence emission of said cells with a channel peak height location of emission signals as shown by numerical readout or by graphic display from the flow cytometer.

24. The process of claim 23, wherein a fixed and stained malaria-infected blood sample is used as a biological standard to calibrate photomultiplier tubes of said flow cytometer by proper peak alignment.

25. The process of claim 24, wherein nucleated blood cells are used to calibrate photomultiplier tubes of said flow cytometer by positioning said cells so as to provide suitable resolution of micronucleated cells and red blood cells.

26. The process of claim 24, wherein intrinsic nucleated cells of leukocyte-lineage serve as a stain and emission standard and are properly positioned at the upper end of the dynamic range, so as to provide suitable resolution of micronucleated cells and red blood cells.

27. The calibration process as defined in claim 1, step h, wherein photomultiplier tube gains are set to specific ranges so as to position microspheres and the biological standards at specific positions within the dynamic range, such that red blood cells are located near the origin and nucleated cells are at the opposite corner region of a red fluoescence versus blue fluorescence bivariate graph.

28. The monitoring process as defined in claim 1 step i, wherein microspheres or nucleated cells are incorporated into stained blood or bone marrow samples so as to monitor changes in said fluorescence and light scatter properties that might result from plugs or other forms of signal misalignment that could adversely affect the fidelity of data acquisition.

29. The process of claim 28, wherein 6 µm polychromatic microspheres are added to said blood or bone marrow samples in order to evaluate instrument drift in real time during each analysis.

30. The process of claim 28, wherein instrument drift and staining variation are monitored by adding to said samples unique and discernable nucleated cells selected from the group consisting essentially of avian blood cells, fish blood cells, and parasitized mammalian blood cells.

31. The tabulation process as defined in claim 1, step j, wherein the fluorescent emission from the excited blood or bone marrow cells, consisting essentially of polychromatic cells and cells containing micronucleii, is obtained by injecting a sample of said cells into the sheath stream of said flow cytometer, thence passing in single file through the beam produced by the laser in said cytometer, and wherein the filter before the blue-green photomultiplier tube in said cytometer is within the range of from 400 nm to 560 nm, and the filters before the red photomultiplier tube are within the range from 560 nm to 700 nm, with said filters selected from long pass-short pass filter combinations or bandpass filters.

32. The process of claim 31 wherein the filters before the blue-green photomultiplier tube are a 400 nm long pass filter and a 555 nm short pass filter, and the filter before the red photomultiplier tube is a 580 nm long pass filter.

33. The process of claim 31, wherein the steps of acquiring data reflecting the relative number of red blood cells, polychromatic cells, nucleated cells, and micronucleated cells, includes:
   a) signal detection wherein the fluoescent and light scatter properties of said cells are sensed with from one to six photomultiplier tubes or photodiodes in said cytometer;
   b) data acquisition wherein the fluorescence and light scatter signals from micronucleated, polychromatic and nucleated cells can be sensed and amplified by two or more sets of photomultiplier tubes so as to achieve separation and resolution on a bivariate display; and
   c) data storage wherein the photomultiplier signal profiles of said cells are obtained at a rate of 1000 to 5000 cells/second, and data are transmitted to a computer file for data storage and processing.

34. The process of claim 33, wherein the blue fluorescence, red fluorescence and side scatter properties are acquired by three photomultiplier tubes and the light scatter properties of said cells are acquired with a photomultiplier tube or photodiode, and the photomultiplier tube signal profiles of said cells are transmitted to a computer file for data processing.

35. The process of claim 33, wherein the fluorescent signals and light scatter signals are obtained in a form selected from the group consisting of listmode, dual parameter or single parameter files, which is stored in the computer or on a disk for later data processing.

36. The analysis process as defined in claim 1 step k, wherein the changes in the number of cell populations, consisting essentially of micronucleated cells and polychromatic cells, are acquired as list mode files and are analyzed by data processing operations, comprising:
   a) obtaining list mode files ranging from 5000 to 50,000 events from an initial control blood sample wherein signals from said cells are gated on light scatter, side scatter, and red or green fluroescence so as to obtain said cells and exclude red blood cells and nucleated cells;
   b) obtaining list mode data from a final blood sample wherein signals from said cells are gated on light scatter, side scatter, and red or green fluroescence so as to obtain said cells and exclude red blood cells and nucleated cells;
   c) determining the number of polychromatic cells present in each sample relative to the total blood cell population by acquiring a single parameter file in order to adjust for changes in the polychromatic cell distribution relative to the initial values at time=0 hour;
   d) obtaining a polychromatic cell normalization factor (K) by dividing the number of polychromatic cells at time of later sampling ($N_t$) by the number of polychromatic cells at time of initial sampling ($N_o$), where the total cells counted can range from $10^4$ to $10^6$ cells;
   e) using said normalization factor K to obtain a projected initial micronucleated cell count ($T_t$) by dividing the number of micronuclei measured from the initial sample ($MN_o$) by K such that $T_t = MN_o/K$;
   f) subtracting the projected initial number of micronucleated cells from the actual number of micronucleated cells measured from the time of sampling ($A_t$) to give the change in micronucleated cells relative to time=0 hours () such that $\_ = A_t - T_t$.

37. The process of claim 36, wherein list mode files are generated for blood samples obtained at intervals ranging from time=0 hour to 144 hours or longer from the initial dose, in order to evaluate changes in the micronucleated cell populations relative to the initial levels at time=0 hour.

38. The process of claim 36, wherein list mode files are generated for blood samples obtained at time=0 hour and time=96 in order to evaluate changes in the micronucleated cell populations relative to the initial levels at time=0 hour.

39. The process as defined in claim step k, wherein the cells, consisting essentially of micronucleated cells and polychromatic cells, are acquired and analyzed in the dual parameter mode by data processing operations whereupon analysis areas as defined for comparing micronucleus cell data and polychromatic cell from blood obtained from the initial sampling of untreated mice, and from sampling of mice after dosing with a test substance.

40. The process of claim 39, wherein the analysis areas for micronucleated cells and polychromatic cells are located on red fluorescence versus blue fluorescence bivariate graphs in regions that can be defined relative to the location of biological standards selected from the group consisting of *Plasmodium berghei* infected cells, chick red blood cells, fluorescent microspheres, or combinations thereof.

41. The process of claim 39, wherein an analysis area is defined by the contour patterns of blood that was infected with the malarial parasite, *Plasmodium berghei*, and plotted on a dual parameter bivariate graph following data acquisition.

42. The process of claim 39, wherein the analysis area is present on bivariate graphs such that fluorescence and light scatter properties are displayed in a discriminating manner relative to internal or external calibration standards.

43. The process of claim 39, wherein the change in micronucleated cells is obtained by subtracting the number of micronucleated cells in the defined analysis area of the initial blood sample from the number of micronucleated cells in the defined analysis area of the final sample taken following the dosing treatment interval.

44. The process of claim 43, wherein the change in micronucleated cells is obtained by subtracting the number of micronucleated cells in the data obtained for the initial sample from the number in data obtained for the final sample, both samples originating from the same mouse.

45. The process of claim 44, wherein the changes in micronucleated cells is obtained by calculating the mean of the difference (i.e.) from multiple samples taken from untreated mice and subtracting said mean from the comparably calculated mean from multiple samples obtained from mice that were dosed with a test substance.

46. The process as defined in claim 1 step k wherein the changes in the cell populations consist of changes in the number of micronucleated cells which are acquired as single parameter files, and are analyzed by data processing operations such that upper and lower analysis ranges are chosen in order to compare data from the initial blood samples with data from subsequent blood samples.

47. The process of claim 46, wherein the analysis range is defined by the location of the peak for malarial parasite, *Plasmodium berghei*, as obtained from a fluorescence histogram.

* * * * *